US007892825B2

(12) United States Patent
Barr et al.

(10) Patent No.: US 7,892,825 B2
(45) Date of Patent: Feb. 22, 2011

(54) METHOD OF PROTEIN PRODUCTION IN YEAST

(75) Inventors: Philip J. Barr, Oakland, CA (US); Helen L. Gibson, Oakland, CA (US)

(73) Assignee: Arriva Pharmaceuticals, Inc., Alameda, CA (US)

( * ) Notice: Subject to any disclaimer, the term of this patent is extended or adjusted under 35 U.S.C. 154(b) by 0 days.

(21) Appl. No.: 12/217,612

(22) Filed: Jul. 7, 2008

(65) Prior Publication Data

US 2009/0042278 A1 Feb. 12, 2009

Related U.S. Application Data

(62) Division of application No. 10/914,863, filed on Aug. 9, 2004, now Pat. No. 7,419,801.

(60) Provisional application No. 60/493,984, filed on Aug. 8, 2003.

(51) Int. Cl.
*C12N 15/63* (2006.01)
*C12N 1/00* (2006.01)
*C12N 15/11* (2006.01)

(52) U.S. Cl. ............... 435/320.1; 435/254.21; 435/255.1; 536/23.1

(58) Field of Classification Search ............... None
See application file for complete search history.

(56) References Cited

U.S. PATENT DOCUMENTS

| | | | |
|---|---|---|---|
| 4,150,071 A | 4/1979 | Pecina | |
| 4,198,969 A | 4/1980 | Virag | |
| 4,253,468 A | 3/1981 | Lehmbeck | |
| 4,301,970 A | 11/1981 | Craighero | |
| 4,453,542 A | 6/1984 | Hughes | |
| 4,599,311 A | 7/1986 | Kawasaki | |
| 4,620,670 A | 11/1986 | Hughes | |
| 4,711,848 A | 12/1987 | Insley et al. | |
| 4,732,973 A | 3/1988 | Barr et al. | |
| 4,752,576 A | 6/1988 | Brake et al. | |
| 4,775,622 A | 10/1988 | Hitzeman et al. | |
| 4,837,148 A | 6/1989 | Cregg | |
| 4,839,283 A | 6/1989 | Kawasaki et al. | |
| 4,929,555 A | 5/1990 | Cregg et al. | |
| 4,931,373 A | 6/1990 | Kawasaki et al. | |
| 4,940,661 A | 7/1990 | Etcheverry et al. | |
| 5,010,003 A | 4/1991 | Chang et al. | |
| 5,013,652 A | 5/1991 | Stausberg et al. | |
| 5,093,316 A | 3/1992 | Lezdey et al. | |
| 5,114,953 A | 5/1992 | Galardy et al. | |
| 5,134,119 A | 7/1992 | Lezdey et al. | |
| 5,150,071 A | 9/1992 | Bouzidi | |
| 5,166,134 A | 11/1992 | Lezdey et al. | |
| 5,218,091 A | 6/1993 | Kawasaki et al. | |
| 5,256,657 A | 10/1993 | Singh et al. | |
| 5,594,106 A | 1/1997 | Black et al. | |
| 5,618,786 A | 4/1997 | Roosdorp et al. | |
| 5,696,147 A | 12/1997 | Galardy | |
| 5,773,438 A | 6/1998 | Levy et al. | |
| 5,780,440 A | 7/1998 | Lezdey et al. | |
| 5,892,112 A | 4/1999 | Levy et al. | |
| 5,922,569 A | 7/1999 | Heim et al. | |
| 5,972,986 A | 10/1999 | Seibert et al. | |
| 5,993,783 A | 11/1999 | Eljamal et al. | |
| 6,068,994 A | 5/2000 | Barr | |
| 6,103,500 A | 8/2000 | Innis et al. | |
| 6,133,304 A | 10/2000 | Peterson, Jr. et al. | |
| 6,204,012 B1 | 3/2001 | Hellmuth et al. | |
| 6,469,040 B2 | 10/2002 | Seibert et al. | |
| 6,489,308 B1 | 12/2002 | Shapiro | |
| 6,544,497 B2 | 4/2003 | Zhu et al. | |
| 6,693,096 B2 | 2/2004 | Fritz et al. | |
| 6,740,655 B2 | 5/2004 | Magee et al. | |
| 2001/0006939 A1 | 7/2001 | Niven et al. | |
| 2002/0099013 A1 | 7/2002 | Piccariello et al. | |
| 2003/0068280 A1 | 4/2003 | Bannister et al. | |

(Continued)

FOREIGN PATENT DOCUMENTS

EP 0 284 044 A1 9/1988

(Continued)

OTHER PUBLICATIONS

Komeda et al. Construction of protease-deficient *Candida boidinii* strains useful for recombinant protein production: cloning and disruption of proteinase A gene (PEP4) and proteinase B gene (PRB1). Biosci Biotechnol Biochem. Mar. 2002;66(3):628-31.*

Tsalik et al. Curing *Saccharomyces cerevisiae* of the 2 micron plasmid by targeted DNA damage. Yeast. Jun. 30, 1998;14(9):847-52.*

(Continued)

*Primary Examiner*—Michele K Joike
(74) *Attorney, Agent, or Firm*—Arnold & Porter, LLP; Jeffrey P. Bernhardt

(57) ABSTRACT

Vectors, host cells, and methods are provided for the production of proteins in yeast. The vectors generally contain a selection gene, a yeast 2 micron sequence, and a polynucleotide encoding a polypeptide, where the polynucleotide is operably linked to promoter, and where the polynucleotide contains one or more yeast-preferred codons. Host cells are cultured under conditions where, after an initial batch phase, oxygen concentration is kept high and glucose feed is regulated so that the yeast cells stay in respiratory metabolism.

24 Claims, 1 Drawing Sheet

U.S. PATENT DOCUMENTS

| | | | |
|---|---|---|---|
| 2003/0073217 | A1 | 4/2003 | Barr et al. |
| 2003/0078276 | A1 | 4/2003 | Andrianjara et al. |
| 2003/0211548 | A1 | 11/2003 | Packard et al. |

FOREIGN PATENT DOCUMENTS

| | | |
|---|---|---|
| EP | 73654 A | 12/1990 |
| EP | 0 648 838 | 7/2002 |
| EP | 1 226 119 | 7/2002 |
| EP | 1 226 136 | 7/2002 |
| EP | 1 047 450 | 10/2002 |
| WO | WO 84/04538 | 11/1984 |
| WO | WO 92/09282 | 6/1992 |
| WO | WO 92/09556 | 6/1992 |
| WO | WO 92/09563 | 6/1992 |
| WO | WO 93/13741 | 7/1993 |
| WO | WO 94/02446 | 2/1994 |
| WO | WO 94/21625 | 9/1994 |
| WO | WO 94/22309 | 10/1994 |
| WO | WO 95/09841 | 4/1995 |
| WO | WO 95/19965 | 7/1995 |
| WO | WO 96/16027 | 5/1996 |
| WO | WO 96/32152 | 10/1996 |
| WO | WO 97/42168 | 11/1997 |
| WO | WO 98/07742 | 2/1998 |
| WO | WO 98/14424 | 4/1998 |
| WO | WO 98/16205 | 4/1998 |
| WO | WO 98/43946 | 10/1998 |
| WO | WO 98/47863 | 10/1998 |
| WO | WO 99/32150 | 7/1999 |
| WO | WO 99/44989 | 9/1999 |
| WO | WO 00/34237 | 6/2000 |
| WO | WO 00/54797 | 9/2000 |
| WO | WO 02/50287 | 6/2002 |
| WO | WO 02/053138 | 7/2002 |
| WO | WO 02/064080 | 8/2002 |
| WO | WO 03/068188 | 8/2003 |
| WO | WO 03/075959 | 9/2003 |
| WO | WO 2004/060528 | 7/2004 |
| WO | WO 2004/103364 | 12/2004 |
| WO | WO 2005/003150 | 1/2005 |

OTHER PUBLICATIONS

Hubbard, R.C., et al., "Anti-Neutrophil-Elastase Defenses of the Lower Respiratory Tract in Alpha 1-Antitrypsin Deficiency Directly Augmented with an Aerosol of Alpha 1-Antitrypsin," Annals of Internal Medicine, 111(3): 206-212, 1989.

He, J.Q., et al., "Pharmacogenomics of COPD,"Current Pharmacogenomics, 1(4): 229-243, 2003.

Bennetzen, et al., "Codon Selection in Yeast," The Journal of Biological Chemistry, 257(6): 3026-3031, 1982.

Tamer, et al., "Production and Recovery of Recombinant Protease Inhibitor Alpha-1-Antitrypsin, Enzyme and Microbial Technology," 29: 611-620, 2001.

Russell, et al., "Nucleotide Sequence of the Yeast Alcohol Dehyorgenase II Gene," The Journal of Biological Chemistry, 258(4): 2674-2682, 1983.

Barr, et al., "Yeast Genetic Engineering," Chap. 6, Butterworths, 1989.

Broach, et al., "Transformation in Yeast: Development of a Hybrid Cloning Vector and Isolation of the CAN1 Gene," Gene, 8:121-133, 1979.

Pearson, et al., "Improved Tools for Biological Sequence Comparison," Proceedings of the National Academy of Science, 85: 244-2448, 1988.

Tuite, M.F., et al., "Regulated High Efficiency Expression of Human Interferon-Alpha in *Saccharomyces cerevisiae*," The EMBO Journal, 1(5): 603-608, 1982.

Kurachi, K., et al., "Cloning and Sequence ofcDNA Coding for $\alpha_1$-Antitrypsin," Proc Natl Acad Sci USA, Biochemistry, 78(11): 6826-6830, 1981.

Kurjan, J., et al., "Structure of a Yeast Pheromone Gene (MF α): A Putative α-Factor Precursor Contains Four Tandem Copies of Mature α-Factor," Cell, 30: 933-943, 1982.

Zakian, V.A., et al., "Construction, Replication, and Chromatin Structure of TRP1 R1 Circle, a Multiple-Copy Synthetic Plasmid Derived from *Saccharomyces cerevisiae* Chromosomal DNA", Molecular and Cellular Biology, 2(3): 221-232, 1982.

Dayhoff, et al., "A Model of Evolutionary Change in Proteins," Atlas of Protein Sequence and Structure, National Biomedical Research Foundation, 5(3):345-358,1979.

Hein, J.. "Unified Approach to Alignment and Phylogenies," Methods in Enzymology, 183: 626-645, 1990.

Higgins, D.G., et al., "Fast and Sensitive Multiple Sequence Alignments on a Microcomputer," CABIOS Communications, 5(2): 151-153, 1989.

Jones, E.W., "Vacuolar Proteases in Yeast *Saccharomyces cerevisiae*," Methods in Enzymology, 85(31):372-386, 1990.

Kurtz, M.B., et al., "Integrative Transformation of *Candida albicans*, Using a Cloned Candida ADE2 Gene," Molecular and Cellular Biology, 6(1): 142-149, 1986.

Kunze, et al., "Transformation of the Industrially Important Yeasts *Candida maltosa* and *Pichia guilliermondii*," Journal of Basic Microbiology, 25(2): 141-144, 1984.

Myers, E.W., et al. "Optimal Alignments in Linear Space," CABIOS Communications, 4(1): 11-17, 1988.

Robinson, D.F., "Comparison of Labeled Trees with Valency Three," Journal of Combinational Theory, 11: 105-119,1971.

Saitou, N., et al., "The Neighbor-Joining Method: A new Method for Reconstructing Phylogenetic Trees," Molecular Biology and Evolution, pp. 406-425, 1987.

Wilbur, W.J., et al., "Rapid Similarity Searches of Nucliec Acid and Protein Data Banks," Proc Natl Acad of Sci USA, 80: 726-730, 1983.

Zou, et al., "Maspin, a Serpin with Tumor-Suppressing Activity in Human Mamary Epithelial Cells," Science, 263: 526-529, 1994.

Gleeson, M.A., et al., "Transformation of the Methylotrophic Yeast *Hansenula polymorpha*," Journal of General Microbiology, 132: 3459-3465, 1986.

Roggenkamp, R., et al., "Transformation of the Methylotrophic Yeast *Hansenula polymorpha* by Autonomous Replication and Integration Vectors," Mol. Gen. Genet., 202: 302-308, 1986.

Das, et al., "Transformation of *Kluyveromyces fragilis*," Journal of Bacteriology, 158(3): 1165-1167, 1984.

De Louvencourt, et al., "Transformation of *Kluyveromyces lactic* by Killer Plasmid DNA," Journal of Bacteriology, 154(2): 737-742, 1983.

Van Den Berg, et al., "*Kluyveromyces* as a Host of Herterologous Gene Expression: Expression and Secretion of'Prochymosin", Biotechnology, 8: 135-140, 1990.

Cregg, et al., "*Pichia pastoris* as a Host System for Transformations," Molecular and Cellular Biology, 5(12): 3376-3385, 1985.

Hinnen, A., et al., "Transformation of Yeast," Proc. Natl. Acad of Sci. USA, Genetics, 75(4): 1929-1933, 1978.

Ito, H., et al., "Transformation of Intact Yeast Cells Treated with Alkali Cations", Journal of Bacteriology, 153(1): 163-168, 1983.

Davidow, L.S., et al., "Integrative Transformation of the Yeast *Yarrowia lipolytica*," Current Genetics, 10: 39-48, 1985.

Gaillardin, et al., "Integrative transformation of the Yeast *Yarrowia lipolytica*," Current Genetics, 10: 49-58, 1985.

Winkler, M., "Time-Profiling and Enviromental Design in Computer-Controlled Fermentation and Enzyme Production," Genetically-Engineered Proteins and Enzymes from Yeast: Production Control, Ellis Horwood Limited, Chp. 4 and 5, pp. 96-184, 1991.

Schiestl, et al., "High Efficiency Transformation of Intact Yeast Cells Using Single Stranded Nucleic Acids as a Carrier," Current Genetics, 16: 339-346, 1989.

Jones, E.W., "Tackling the Protease Problem in *Saccharomyces cerevisiae*," Methods in Enzymology, 194: 428-453, 1991.

du Preez, J.C., et al., "Transcriptional Repression of ADH2-Regulated β-xylanase Production by Ethanol in Recombinant Strains of *Saccharomyces cerevisiae*," FEMS Yeast Research, 1: 233-240, 2001.

European Search Report dated Jan. 9, 2007.
Kaslow, D.C., et al., "Production, Purification and Immunogenicity of a Malaria Transmission-Blocking Vaccine Candidate: TBV25H Expressed in Yeast and Purified Using Nickel-NTA Agarose," Nature Publishing Group, 12: 494-499, 1994.
Noronha, S.B., et al., "Transition Phase in the Production of Recombinant Proteins in Yeast Under the ADH2 Promoter: An Important Step for Reproducible Manufacturing of a Malaria Transmission Blocking Vaccine Candidate," Journal of Individual Microbiology & Biotechnology, 20:192-199, 1998.
O'Connor, G.M., "Design and Evaluation of Control Strategies for High Cell Density Fermentations," Biotechnology and Bioengineering, 39 (3):293-304, 1992.
Sabin, E.A., et al., "High-Level Expression and in Vivo Processing of Chimeric Ubiquitin Fusion Proteins in *Saccharomyces cervisiae*," Bio/Technology, 7: 705-709, 1989.
Amiali, et al., "High Nisin Z Production by *Lactococcus lactis* UL719 in Whey Permeate with Aeration," World Journal of Microbiology & Biotechnology, 14: 887-894, 1998.
Jennings, Thomas A., "Lyophilization: Introduction and Basic Principles," Interpharm Press, pp. 42-44, 261-279, 1999.
Carlson, J.A., et al., "Accumulation of PiZ $\alpha_1$-Antitrypsin Causes Liver Damage in Transgenic Mice," J. Clin. Invest., 83:1183-1190, 1989.
Carrell, R.W., et al., Structure and Variation of Human Alpha 1-Antitrypsin, *Nature*, 298: 329-334, 1982.
Carter, P., et al., "Improved Oligonucleotide Site-Directed Mutagenesis Using M13 Vectors," Nucleic Acids Research, 13(12): 4431-4443, 1985.
Nail, S., et al., "Development and Manufacture of Protein Pharmaceuticals," Pharmaceutical Biotechnology, 14: 65-66, 2002.
Dycaico, et al., "Neonatal Hepatitis Induced by $\alpha_1$-Antitrypsin: A Transgenic Mouse Model," Science, 242: 1409-1412, 1988.
Gadek, et al., "$\alpha_1$-Antitrypsin Deficiency," The Metabolic Basis of Inherited Diesease, Stanbury, J.B. et al., eds., McGraw-Hill, New York, pp. 1450-1467, 1982.
GenBank Accession No. AAB59375, Host: NCBI, Database: Genbank, 2009.
Ash, M., et al., Handbook of Pharmaceuetical Additives, 2nd Edition, Synapse Information Resources, Inc., pp. 797-798, 2002.
Hunnighake, G.W., et al., "Cigarette Smoking and Lung Destruction: Accumulation of Neutrophils in the Lungs of Cigarette Smokers," Am. Rev. Respir. Dis., 128: 833-838, 1983.
Lomas, D.A., et al., "The Mechanism of Z $\alpha_1$-Antitrypsin Accumulation in the Liver," Nature, 357: 605-607, 1992.
Neddleman, S.B., et al., "A General Method Applicable to the Search for Similarities in the Amino Acid Sequence of Two Proteins," J. Mol. Biol., 48: 443-453, 1970.
Carpenter, J.F., et al., Rational Design of Stable Lyophilized Protein Formulations: Theory and Practice, Rational Design of Stable Protein Formulations Theory and Practice, 13: 109-133, 2002.
Smith, T.F., et al., "Comparison of Biosequences," Adv. in Appl. Math., 2: 482-489, 1981.
Smith, et al., "Pulmonary Deposition and Clearance of Aerosolized Alpha-1-Proteinase Inhibitor Administered to Dogs and to Sheep," J. Clin, Invest., 84: 1145-1154, 1989.
Randolph, T.W., et al., "Surfactant-Protein Interactions," Rational Design of Stable Protein Formulations: Theory and Practice, Pharmaceutical Biotechnology, Kluwer Academic/Plenum Publishers, pp. 159-175, 2002.
Wells, J.A., Cassette Mutagenesis: An Efficient Method for Generation of Multiple Mutations at Defined Sites, et al., Gene, 34: 315-323, 1985.

Wells, J.A., et al., Importance of Hydrogen-Bond Formation in Stabilizing the Transition State of Sutilisin, Philos Trans. R. Soc. London, 317: 415-423, 1986.
Wu, Y., et al., "A Lag in Intracellular Degradation of Mutant $\alpha 1$-Antitrypsin Correlates with the Liver Disease Phenotype in Homoqygous PiZZ $\alpha 1$-Antitrypsin Deficiency," Proc. Natl. Acad. Sci., 91: 9014-9018, 1994.
Zoller, et al., "Oligonucleotide-Directed Mutagenesis.Using M13-Derived Vectors: An Efficient and General Procedure for the Production of Point Mutations in any Fragment of DNA," Nucleic Acids Research, 10(20): 6487-6500, 1982.
Beatty, et al., "Kinetics of Association of Serine Proteinases with Native and Oxidized Alpha-1-Proteinase Inhibitor and Alpha-1-Antichymotrypsin," J. Biol. Chem., 255(9): 3931-3934, 1980.
Travis, et al., "Isolation and Properties of Recombinant DNA Produced Variants of Human Alpha1-Proteinase Inhibitor," Journal of Biological Cheimstry, 260(7): 4384-4389, 1985.
Vemuri, et al., "Stability and Characterization of Protein and Peptide Drugs: Case Histories," Wang and Pearlman, Plenum Press, NY, Chap. 9 pp. 263-285, 1993.
Vemuri, S., et al., "Effect of Cryoprotectants on Freezing, Lyophilization, and Storage of Lyophilized Recombinant Alpha1-Antitrypsin Formulations," PDA Journal of Pharmaceutical Science and Technology, 48(5): 241-246, 1994.
Pemberton, P., et al., "Inhaled recombinant Alpha 1-Antitrypsin Ameliorates Cigarette Smoke-Induced Emphysema in the Mouse," COPD: Journal of Chronic Obstructive Pulmonary Disease, 3: 101-108, 2006.
Stockley, et al., "Therapeutic Efficacy of Alpha-1 Antitrypsin (AAT) Augmentation Therapy on the Loss of Lung Tissue: An Integrated Analysis," *European Respiratory Society*, Abstract, 2008.
Stolk, et al., "Progression Parameters for Emphysema: A Clinical Investigation," *Respiratory Medicine*, 101: 1924-1930, 2007.
Hercz, A., "Proteolytic Cleavages in Alpha-One Antitrypsin and Microheterogeneity,"*Biochem. Biophys. Res. Comm.*, 128(1): 199-203, 1985.
Schasteen, C.S., et al., "Synthetic Peptide Inhibitors of Complement Serine Proteases—Significant Increase in Inhibitor Potency Provides Further Support for the Functional Equivalence Hypothesis," *Molecular Immunology*, 28(1/2): 472-479, 1991.
Churg, et al., "Proteases and Emphysema," *Current Opinion in Pulmonary Medicine*, 11: 153-159, 2005.
Huang, et al., "Expression and Purification of Functional Human Alpha1-Antitrypsin from Cultured Plant Cells," *Biotechology Prog*, 17: 126-33, 2001.
Rabe, "Outcome Measures in COPD," *Primary Care Respiratory Journal*, 13: 177-178, 2004.
Rosenerg, et al., "Synthesis in Yeast of a Functional Oxidation-Resistant Mutant of Human Alpha1-Antitrypsin," *Nature*, 312: 77-80, 1984.
Shapiro, "Envolving Concepts in the Pathogenesis of Chronic Obstructive Pulmonary Disease," *Clinics in Chest Medicine*, 21(4):621-632, 2000.
Terashima, et al., "Production of Functional Human Alpha1-Antitrypsin by Plant Cell Culture," *Appl. Microbiol. Biotechnol.*, 52: 516-523, 1999.
Barnes, P.J., "Novel Approaches and Targets for Treatment of Chronic Obstructive Pulmonary Disease," *Am.J. Respir. Crit. Care Med.*, 160:S72-S79, 1999.
Roche, N., et al., "Current Issues in the Management of Chronic Obstructive Pulmonary Diseases," *Respirology*, 2: 215-229, 1997.

\* cited by examiner

Plasmid pYEP829

METHOD OF PROTEIN PRODUCTION IN YEAST

RELATED APPLICATION DATA

The present application is a divisional of, and claims priority under 35 USC §120 to U.S. application Ser. No. 10/914,863 filed Aug. 9, 2004 now U.S. Pat. No. 7,419,801, which claims priority under USC §119(e) to U.S. Provisional Application 60/493,984 filed Aug. 8, 2003, the disclosures of which are hereby incorporated by reference in its entirety.

REFERENCE TO A SEQUENCE LISTING

The instant application contains a Sequence Listing which has been submitted via EFS-Web and is hereby incorporated by reference in its entirety. Said ASCII copy, created on Jul. 12, 2010, is named ARR0012_ST25.TXT, and is 23,389 bytes in size.

STATEMENT REGARDING FEDERALLY SPONSORED RESEARCH OR DEVELOPMENT

Not Applicable.

FIELD OF THE INVENTION

The present invention provides vectors, host cells, and methods for the production of proteins in yeast. The proteins that may thus be produced, for example, protease inhibitors, have a wide variety of activities, including activities useful for medical, veterinary, and agricultural purposes. The present invention therefore relates to the fields of molecular biology, recombinant DNA technology, medicine, animal health, and agriculture.

BACKGROUND OF THE INVENTION

Yeast are commonly used for expression of heterologous proteins, and have several advantages as an expression system. Yeast are a simple and well-characterized eukaryotic organism, and yeast may be readily manipulated by present genetic engineering techniques.

Recent genetic engineering and fermentation efforts in yeast have been directed at methods to produce human proteins in useable form in yeast at commercially viable levels of production, and with a minimum of modification of the protein. Such efforts are described in, e.g., U.S. Pat. Nos. 4,775,622; 4,940,661; 5,010,003; 5,013,652; 5,922,569; 6,204,012; and 6,103,500.

Among other proteins, human alpha 1-antitrypsin (hAAT) has been cloned and produced in yeast. See, e.g., U.S. Pat. Nos. 4,752,576 and 4,839,283. However, it has heretofore been difficult to produce AAT in yeast in high concentrations in soluble form. Therefore, a need exists in the art for methods of producing proteins, such as soluble AAT, in yeast in high concentrations.

BRIEF SUMMARY OF THE INVENTION

In one aspect, the invention provides vectors. In some embodiments, vectors of the invention include a selection gene, a yeast 2 micron sequence, and a polynucleotide encoding a polypeptide, where the polynucleotide is operably linked to an alcohol dehydrogenase 2 promoter. In some of these embodiments, the polynucleotide includes one or more yeast-preferred codons substituted for naturally occurring codons. In some embodiments, the vector does not propagate and/or amplify in a bacterial host cell. In some embodiments, the selection gene is a URA3 gene. In some embodiments, the polypeptide comprises a protease inhibitor or functionally active portion thereof. In some of the latter embodiments the protease inhibitor is alpha 1-antitrypsin, maspin, or alpha 1-antichymotrypsin.

In another aspect, the invention provides yeast cells transformed with vectors of the invention. In some embodiments, the yeast cell is of the genus *Saccharoinyces*.

In some embodiments, the yeast cell is cir°. In some of these embodiments, the yeast cell is protease deficient and/or is strain BJ2168[°]TRP.

In another aspect, the invention provides methods for producing a desired polypeptide. In some embodiments, methods of the invention include culturing a yeast cell capable of expressing the desired polypeptide, where the yeast cell contains a polynucleotide that includes a nucleotide sequence with a yeast 2 micron DNA sequence, and a nucleotide sequence encoding the desired polypeptide operably linked to a yeast alcohol dehydrogenase 2 promoter, where the polynucleotide includes one or more yeast-preferred codons substituted for naturally occurring codons, in a fermentative process that includes a batch phase and a fed batch phase under conditions such that dissolved oxygen is continually present in the culture medium throughout the process, where the rate of glucose feed during the fed batch phase is monitored and adjusted so that the cells are maintained in a respiratory state. In some embodiments, the methods further include isolating the desired polypeptide on completion of the fed batch phase. In some of these embodiments, the host yeast cell is a cir° protease-deficient trp revertant cell.

In some embodiments the final concentration in the yeast culture of the desired polypeptide is at least about 1 gm per liter, 2 gm per liter, or 4 gm per liter. In some embodiments, the desired polypeptide is transferrin or human serum albumin, or a fusion protein thereof. In other embodiments, the desired polypeptide is a protease inhibitor or functionally active portion thereof. In some of these embodiments, the protease inhibitor is alpha 1-antitrypsin, alpha 1-antichymotrypsin, or maspin. In some embodiments, the desired polypeptide is a fusion polypeptide. In some of these embodiments, the desired polypeptide is a fusion polypeptide of protease inhibitors or functionally active portions thereof, such as a fusion protein that includes alpha 1-antitrypsin or functionally active portion thereof. In some embodiments of the methods of the invention, the nucleotide sequence encoding the desired polypeptide is further operably linked to an alcohol dehydrogenase 2 terminator. In some embodiments, dissolved oxygen is continually present in the culture medium at a concentration of greater than or equal to about 50%. In some embodiments, the polynucleotide further includes a polynucleotide encoding a yeast URA3 polypeptide. In some embodiments, the yeast cell is of the genus *Saccharomyces*, such as the strain BJ2168-[cir°]TRP revertant. In some embodiments, the glucose provides about 100% of the oxidizable substrate for respiration. In one embodiment of the methods of the invention, the polynucleotide further includes a signal sequence operably linked to the yeast alcohol dehydrogenase 2 promoter.

DETAILED DESCRIPTION OF THE INVENTION

Figure 1:
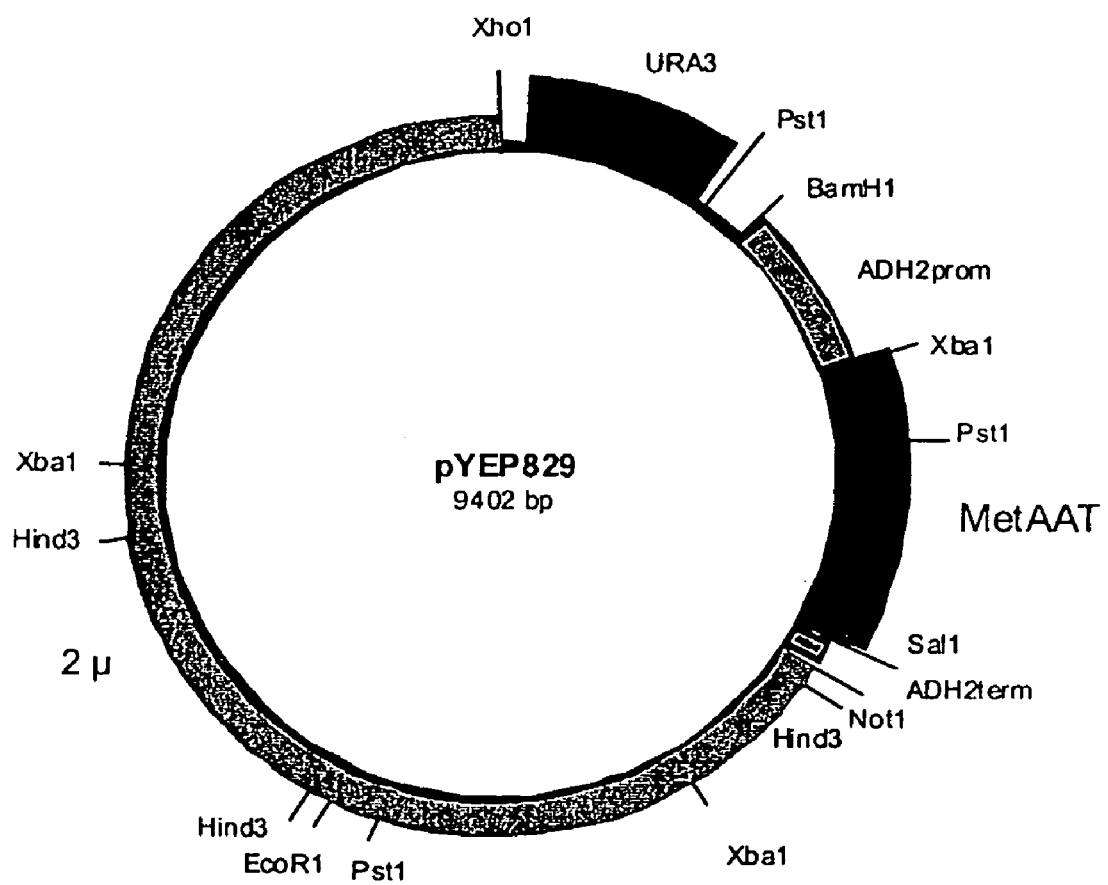
FIG. 1 illustrates the expression vector pYEP829.

The invention concerns compositions and methods for production of polypeptides in yeast transformed with a plasmid, where the plasmid to be used is an episomal expression plasmid and includes a yeast promoter and terminator, a selection gene, the gene for the polypeptide desired to be produced, optionally containing one or more yeast preferred codons that replace naturally-occurring native codons, and an origin of replication such as the 2 micron DNA sequence of yeast plasmid. Preferably, the yeast promoter is a regulated promoter, e.g., the ADH2 promoter; generally in the terminator will match the promoter, e.g., the ADH terminator. In some embodiments the plasmid may also contain a yeast signal (leader) sequence, if it is desired that the polypeptide be secreted extracellularly; however, for many polypeptides, e.g., AAT or fusion proteins of AAT with another protease, a leader sequence is not used as it is desirable that the polypeptide be maintained intracellularly in order to avoid excessive glycosylation. In some embodiments, the plasmid may also be unable to propagate and/or amplify in a bacterial host cell, e.g., because it is substantially free of bacterial sequences required for propagation and/or amplification in a bacterial cell. The plasmid is introduced into an appropriate yeast strain; in some embodiments this is a circle-zero (cir°), protease-deficient yeast strain; in some embodiments the strain contains endogenous yeast plasmid and is cured of endogenous plasmids after transformation. The transformed yeast may be selected by growth on a medium appropriate for the selectable marker of the plasmid, for example, a uracil-deficient medium. In productive fermentation, if a regulated promoter is used, e.g., the ADH2 promoter, the promoter can be regulated to repress recombinant polypeptide synthesis. In embodiments in which the ADH2 promoter is used, production of the protein under control of the promoter is repressed in high glucose levels, providing for continuous expression under glucose-limited growth conditions. The fed batch fermentation process described here allows for regulation of the amount of glucose provided to the yeast culture and thus, control of protein expression.

Definitions and General References

As used herein, a "polynucleotide" is a polymeric form of nucleotides of any length, which contain deoxyribonucleotides, ribonucleotides, and/or their analogs. The terms "polynucleotide" and "nucleotide" as used herein are used interchangeably. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. The use of uracil as a substitute for thymine in a deoxyribonucleic acid is also considered an analogous form of pyrimidine. Although conventional sugars and bases will be used in applying the method of the invention, substitution of analogous forms of sugars, purines and pyrimidines can be advantageous in designing a final product, as can alternative backbone structures like a polyamide backbone.

By "preferred yeast codons" or "yeast preferred codon" is meant codons containing nucleotide bases that have been observed more frequently than other possible codon triplets to encode particular amino acids in yeast. Preferred yeast codons and their use are well-known in the art and are described, inter alia, by Bennetzen and Hall, *J. Biol. Chem.* 257:3026 (1982).

The term "recombinant" polynucleotide (and by analogy, a "recombinant" polypeptide produced by the expression of a recombinant polynucleotide) is one which is not naturally occurring or is made by the artificial combination of two otherwise separated segments of sequence by chemical synthesis means or the artificial manipulation of isolated segments of polynucleotides, e.g., by genetic engineering techniques. Thus, the term "recombinant" polynucleotide as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, carboxylation, phosphorylation, ubiquitination, pegylation or any other manipulation or modification, such as conjugation with a labeling component. Also included within the definition are, for example, polypeptides containing one or more analogs of an amino acid (including, for example, unnatural amino acids, etc.), as well as other modifications. Such modifications are well known; see, e.g., Molecular Cloning: A Laboratory Manual, 2nd ed., Vol. 1-3, ed. Sambrook, et al., Cold Spring Harbor Laboratory Press (1989) or Current Protocols in Molecular Biology, ed. F. Ausubel et al., Greene Publishing and Wiley-Interscience: New York (1987 and periodic updates).

A polynucleotide is said to "encode" a polypeptide if, in its native state or when manipulated by methods well known to those skilled in the art, it can be transcribed and/or translated to produce the polypeptide.

A "fusion protein" is a single polypeptide comprising regions from two or more different proteins. The regions normally exist in or as separate proteins and are brought together in the fusion protein. They may be linked together so that the amino acid sequence of one begins where the amino acid sequence of the other ends, or they may be linked via linker amino acids which are not normally a part of the constituent proteins. They may be linked in any manner, such as through amide bonds, disulfide bonds, etc. A fusion protein may contain more than one copy of any of its constituent proteins or regions. The constituent proteins or regions may include the entire amino acid sequences of the proteins or portions of the amino acid sequences. As is apparent from the definition of "protein," above, the protein may be in branched form; e.g., the side chain of one amino acid in one chain may be linked to the side chain of another, terminal amino acid in another chain by any of a variety of methods known to those of skill in the art (for example, disulfide bond formation). Alternatively, non-terminal amino acids of different chains may also be linked by intermolecular bonds between side chains (e.g., disulfide bonds) to form a branched protein.

As used herein, the term "vector" refers to a polynucleotide molecule capable of transporting another polynucleotide to which it has been linked and can include a plasmid, cosmid or viral vector. The term includes vectors that function primarily for insertion of a polynucleotide molecule into a cell, replication vectors that function primarily for the replication of polynucleotide, and expression vectors that function for transcription and/or translation of the DNA or RNA. Also included are vectors that provide more than one of the above functions. The vector can be capable of autonomous replication or it can integrate into a host DNA. Viral vectors include, e.g., replication defective retroviruses, adenoviruses and adeno-associated viruses.

A vector can include nucleic acid coding for a polypeptide of the invention in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of polypeptide desired, and the like. The expression vectors of the invention can be introduced into host cells to thereby produce proteins or polypeptides, including fusion proteins or polypeptides, encoded by nucleic acids as described herein.

The recombinant expression vectors of the invention can be designed for expression of the proteins of the invention in yeast cells. Methods of expressing proteins in yeast, such as *Saccharomyces cerevisiae, Pichia pastoris, Hansenula polymorpha*, and *Kluyveromyces lactis*, are well-known in the art.

A "host cell" includes an individual cell or cell culture which can be or has been a recipient for vector(s) or for incorporation of polynucleotide molecules and/or proteins. In methods of the present invention, a host cell can be a yeast cell. Other suitable host cells are known to those skilled in the art. Host cells include progeny of a single host cell, and the progeny may not necessarily be completely identical (in morphology or in genomic of total DNA complement) to the original parent cell due to natural, accidental, or deliberate mutation.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, lithium acetate transformation, DEAE-dextran-mediated transfection, lipofection, or electroporation A "signal sequence," also known as a "leader sequence," is a short amino acid sequence that directs newly synthesized secretory or membrane proteins to and through cellular membranes such as the endoplasmic reticulum. Signal sequences are typically in the N-terminal portion of a polypeptide and are cleaved after the polypeptide has crossed the membrane.

"A," "an," and "the" include one or more.

As is well-established in the art (i.e., in accordance with well established legal principles), and as used herein, "comprising" means "including."

The practice of the present invention will employ, unless otherwise indicated, conventional techniques of molecular biology (including recombinant DNA techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology", e.g., Vols. 185, ed. by D. V Goeddel, 1991 (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991); "Yeast Genetic Engineering" (P. J. Barr et al., eds., Butterworths, Boston, 1989).

These techniques are applicable to the production of the polynucleotides, host cells, and proteins of the invention, and, as such, are to be considered when contemplating these inventive aspects. Particularly useful systems for individual aspects will be discussed below.

All publications, patents and patent applications cited herein are hereby incorporated by reference in their entirety for all purposes to the same extent as if each individual publication, patent or patent application were specifically and individually indicated to be so incorporated by reference.

I. Introduction

The invention provides a yeast-based system for protein production. Yeast are transformed with a plasmid, where the plasmid to be used is an episomal expression plasmid and includes a yeast promoter and terminator, a selection gene, the gene for the polypeptide desired to be produced, optionally containing yeast preferred codons, and an origin of replication such as provided by the 2 micron DNA sequence of yeast plasmid. Preferably, the yeast promoter is a regulated promoter; generally in the terminator will match the promoter. In some embodiments the plasmid may also contain a yeast signal (leader) sequence, if it is desired that the polypeptide be secreted extracellularly; however, for many polypeptides a leader sequence is not used as it is desirable that the polypeptide be maintained intracellularly in order to avoid excessive glycosylation. In some embodiments, the plasmid may also be unable to propagate and/or amplify in bacterial host cells, e.g., it may partially or completely lack bacterial sequences required for propagation and/or amplification. The plasmid is introduced into an appropriate yeast strain; in some embodiments this is a circle-zero (cir°), protease-deficient yeast strain; in some embodiments this is a yeast strain that contains an endogenous plasmid and is then cured of endogenous yeast plasmids. The transformed yeast may be selected by growth on a medium appropriate for the selectable marker of the plasmid, for example, a uracil-deficient medium. In fermentation, if a regulated promoter is used, the promoter can be regulated to repress recombinant polypeptide synthesis, allowing biomass to accumulate followed by protein production when the promoter is derepressed. Such a fed batch fermentation process described here allows for a dense culture to be achieved while maintaining aerobic conditions and high levels of recombinant polypeptide expression. The use of this production method produces strikingly high yields of recombinant polypeptides in yeast in soluble form; e.g., recombinant alpha 1-antitrypsin (rAAT) is produced at levels in the final culture medium of between about 3 and about 5 g/L, recombinant maspin is produced at a level of about 2.2 g/L, and recombinant alpha 1-antichymotrypsin (rACT) is produced at a level of about 0.75-0.9 g/L. As is understood in the art, yields may also be expressed as g protein/g wet weight of biomass, g protein/g dry weight of biomass, or g protein/OD unit.

In some embodiments, the compositions and methods provided by the invention for production of polypeptides (e.g., recombinant alpha 1-antitrypsin, maspin, or alpha 1-antichymotrypsin) utilizes a plasmid that contains a 2 micron DNA of yeast plasmid, a glucose-regulated promoter from the alcohol dehydrogenase 2 (ADH2) gene of S. cerevisiae to drive expression of recombinant polypeptide from a chemically synthesized coding sequence containing one or more yeast-preferred codons, a ADH2 terminator for efficient protein chain termination, and a selection gene (e.g., the URA3 gene to allow growth in a uracil-free medium). In some embodiments the plasmid further is unable to amplify and/or propagate in bacterial host cells. The plasmid is transformed into a circle-zero (cir°), protease-deficient yeast strain. The transformed yeast may be selected by growth on, e.g., a uracil-deficient medium, or other medium appropriate for the selectable marker of the plasmid. In productive fermentation, the ADH2 promoter will repress recombinant polypeptide synthesis in high glucose levels and provide for continuous expression under glucose-limiting growth conditions. In these embodiments, the techniques employed allow a dense culture (from about 20 to about 50% biomass) to be achieved while maintaining aerobic conditions and high levels of recombinant polypeptide expression.

The expression vector can be generated from two fragments assembled separately in small, manageable vectors and then ligated and transformed directly into yeast. This method eliminates the need for bacterial sequences required for an *Escherichia coli* shuttle vectors, e.g., origins of replication and/or selectable marker genes. The recombinant polypeptide may be expressed intracellularly to avoid hyperglycosylation of the polypeptide in the secretory pathway (e.g., to avoid immunogenic response to the recombinant protein), or, in some embodiments, e.g., proteins that lack glycosylation sites such as human serum albumin, addition of a signal (leader) sequence allows expression extracellularly.

Strikingly, it has now been found that when the plasmid constructed according to the above criteria, containing an ADH2 promoter and terminator, URA3 gene for a selectable marker, a yeast two micron DNA sequence, and human AAT gene substituted with one or more yeast-preferred codons, is grown according to the conditions described herein, yields of AAT are about 3 to about 5 g/L, about threefold higher than expected from previous reports (see, e.g., Tamer and Chisti, *Enzyme and Microbial Technology* 29:611-620 (2001)). See, e.g., Example 3.

For production, an inoculum is used for initiating fermentation in a shake flask, the shake flask is used to start seed fermentation for increasing yeast biomass, and finally the production fermentor is used to maximize expression and yield of the recombinant polypeptide. Glucose concentrations are regulated as described herein to maximize production. Upon conclusion of fermentation, the cells may be separated from fermentation medium, lysed, and the lysate clarified. In some embodiments of the invention, various methods of purification may then be used to purify the recombinant polypeptide to the desired level of purity.

II. Yeast Expression Plasmids

A. Promoter and Terminator Sequences

A yeast promoter is a DNA sequence that is capable of binding yeast RNA polymerase and initiating the downstream (5'-3') transcription of a coding sequence (e.g. DNA encoding AAT or other recombinant polypeptide or fusion protein) into mRNA. The promoter herein will have a transcription initiation region that is usually placed proximal to the 5' end of the coding sequence. This transcription initiation region usually includes an RNA polymerase binding site (the "TATA box") and a transcription initiation site. A yeast promoter herein may also have a second domain called an upstream activator sequence (UAS), that, if present, is usually distal to the structural gene (i.e., further upstream) relative to the transcription initiation region. The UAS also governs regulation of expression. Regulated expression may be either positive or negative, thereby either enhancing or reducing transcription as desired.

Suitable yeast promoters are for example alcohol dehydrogenase (ADH1 or ADH2), enolase, glyceraldehyde-3-phosphate dehydrogenase (GAPDH, including shortened constitutive versions thereof, e.g. GAPFL and others known to those of skill in the art), glucose-6-phosphate dehydrogenase, glucose-6-phosphate isomerase, triosephosphate isomerase (TPI), phosphofructokinase, glucokinase, 3-phosphoglycerate mutase, hexokinase, phosphofructokinase, and pyruvate kinase, or other genes such as acid phosphatase, beta-actin, alpha-amylase, heat shock proteins, metallothioneins (e.g., CUP-1). Other suitable promoters for use in yeast expression are further described in Hitzeman et al. EP 73,657A.

Any convenient transcriptional termination sequence may be employed that is operative with the transcriptional initiation sequence. For example, the ADH2 termination sequence may be used with the ADH2 promoter. These promoters and terminators are well known and can be produced and used in manners known in the art.

In addition, synthetic promoters that do not occur in nature also function as yeast promoters herein. For example, UAS sequences of one yeast promoter may be joined with the transcription activation of another yeast promoter, creating a hybrid promoter. For examples, see, e.g., U.S. Pat. No. 6,103,500. Also, sequence variants and truncations of naturally-occurring promoters that maintain their activity as promoters may also be used in the vectors of the invention, as will be understood by those of skill in the art.

One embodiment of the invention utilizes the ADH2 promoter and terminator. The ADH2 promoter is a strong promoter that is regulated by glucose concentrations: high glucose concentrations repress recombinant polypeptide synthesis while glucose-limited growth conditions provide for continuous expression of recombinant polypeptide. This can allow large biomass of cells to be produced before polypeptide production is induced, particularly advantageous if the heterologous polypeptide is toxic to yeast. The use of such promoters may also be advantageous in allowing increased solubility of the finally-produced polypeptide. The DNA sequence of the ADH2 promoter and its use is known from, e.g., Russell, et al., *J. Biol. Chem.* 258:2674 (1983) and Barr, et al. (eds), "Yeast Genetic Engineering", Butterworths, 1989, Chapter 6. Accordingly, the ADH2 promoter can be provided by chemical DNA synthesis or isolated from genomic *S. cerevisiae* DNA using suitable DNA probes, e.g. by polymerase chain reaction (PCR).

B. Selection Genes

The plasmids will normally contain a gene or genes (i.e., "selection gene(s)") for one or more markers for selection ("selectable markers") in yeast, where the marker may provide prototrophy to an auxotrophic host, resistance to a biocide, e.g., to antibiotics such as G418, tunicamycin or heavy metal, such as copper or zinc, or other selective technique. Use of selectable markers is described in Broach et al., *Gene* 8:121-133 (1979).

Any selection gene can be used which facilitates the selection for transformants due to the phenotypic expression of the marker protein. Suitable selection genes for yeast are, for example, those coding for proteins conferring antibiotic resistance or, in the case of auxotrophic yeast mutants, genes which complement host lesions. Exemplary selection genes confer, for example, resistance to the antibiotics G418, hygromycin or bleomycin or provide for prototrophy in an auxotrophic yeast mutant, for example the URA3, LEU2, LYS2, HIS3 or TRP1 gene. Use of a selection gene providing prototrophy in an auxotrophic yeast mutant allows selection pressure to be maintained to maximize plasmid copy number at early stages of the production process. An exemplary selection gene for the compositions and methods of the invention is the URA3 gene, which confers prototrophy in a yeast mutant auxotrophic for uracil.

C. 2 micron Sequences

Plasmids of the invention contain an origin of replication. In one embodiment, a 2 micron DNA sequence required for autonomous replication in yeast is utilized, allowing the plasmid to maintain as an extrachromosomal element capable of stable maintenance in a host yeast. In some embodiments, the full-length yeast 2 micron sequence may be used, although functional fragments are contemplated. The full length yeast 2 micron sequence may be cloned from, e.g., an *S. cerevisiae* genomic DNA preparation containing 2 micron DNA; see, e.g., Barr et al. (eds), Chapters 9 and 10.

D. Polynucleotide Coding for the Desired Polypeptide

The polynucleotide coding for the polypeptide to be produced by the methods of the invention may come from any source, naturally occurring, synthetic or combination thereof. Part or all of the polypeptide to be produced may be normally produced by the host yeast cell, or may be not normally produced by the host yeast cell; i.e., a heterologous polypeptide. A naturally occurring sequence used in the polypeptide-coding sequence may be shortened, or otherwise modified to introduce restriction sites. Sequences coding for two or more polypeptides may be joined together to code for a fusion protein.

The polynucleotide may encode a polypeptide that is the same as or different from the native polypeptide. It will be readily understood by those of skill in the art that the native amino acid sequence of a polypeptide is not necessarily required for it to be functionally active. For example, a portion of the polypeptide may be used which retains the desired functionality. Any such sequence may be used, and any additional sequence may be provided, as long as there is requisite functionality. The functionality need not be as high as the native polypeptide, and thus in some instances may be reduced, the same, or even enhanced as compared to the native polypeptide.

In addition, it is well-understood in the art that amino acid changes, including substitutions, deletions, insertions, post-translational modifications, and the use of amino acid analogs, may be made in the native polypeptide or a portion of the native polypeptide without abolishing or significantly reducing the biological or immunological activity of the polypeptide. Single amino acids may be substituted for others with the same charge or hydrophobicity. Other amino acids may be substituted with amino acids of differing charge or hydrophobicity without significantly altering the function of the polypeptide. It is also contemplated to use variants which enhance the function of the polypeptide as compared to native, or wild type, polypeptide. In addition to substitutions, entire portions of the polypeptide may be deleted without abolishing or significantly affecting the basic biological function of the polypeptide, or extra amino acids inserted without abolishing or significantly affecting the function. Such changes are similar to changes that occur by evolution, and the degree of similarity of two polypeptides which differ in amino acid sequence can be determined by a method of quantitative analysis such as that described by Pearson and Lipman (Pearson, W. R., and Lipman, D. J., *Proc. Natl. Acad. Sci. USA* 85:2444-2448, 1998), which compares the homology of amino acid sequences as well as the substitutions of amino acids known to occur frequently in evolutionary families of polypeptides sharing a conserved function.

The polynucleotide coding for the polypeptide, especially heterologous polypeptide, can be isolated e.g. from genomic DNA or a double-stranded DNA (ds cDNA), produced complementary to the corresponding mRNA, or a polynucleotide coding for the amino acid sequence of the polypeptide may be produced by means of chemical and enzymatic processes by means known in the art.

If the desired polypeptide is heterologous, one or more yeast-preferred codons may be substituted for the codons of the native polynucleotide sequence ("naturally occurring codons"). The codons used to direct protein synthesis in mammalian genes can differ significantly from those used for highly expressed homologous yeast genes. It is well known that, because the genetic code is degenerate, several different codons can specify the inclusion of a given amino acid in a growing polypeptide chain. The highly expressed yeast genes contain a high proportion of specific codons which correspond to prominent tRNA species present in the cell. Genes that are expressed less efficiently generally include a more random codon choice for a particular amino acid. See, e.g., Bennetzen et al., *J. Biol. Chem.* 257:3026-3031 (1982). Since mammalian and other genes generally do not utilize these so-called "preferred" yeast codons, expression of such genes is sometimes limited when compared to expression of homologous genes in yeast. Thus, the polynucleotide coding for the desired polypeptide may be modified to substitute yeast-preferred codons for naturally occurring non-yeast preferred codons in the native sequence. See, e.g., Tuite et al., *The EMBO Journal,* 1:603-608, 1982, and PCT Application No. 84/00153 (Pub. No. WO 84/04538). It will be appreciated that any number of non-yeast-preferred codons can be substituted by their yeast-preferred counterparts, i.e., the number of yeast-preferred codon substitutions may range from one to all the codons of the entire sequence. Thus, for example, if it is desired to retard translation of a given part of the coding sequence (for example, to optimize proper folding or post-translational modification, or to increase the proportion of soluble product), one or more non-yeast-preferred codons may be left unaltered so that translation is slowed at the point these codons are encountered. In addition, codons that are already yeast-preferred codons in the original DNA may be substituted by other yeast-preferred codons when there is more than one yeast-preferred codon corresponding to the non-yeast-preferred codon.

Useful polypeptides that may be produced by the compositions and methods of the invention are, for example, enzymes that can be used for the production of nutrients and for performing enzymatic reactions in chemistry, or polypeptides which are useful and valuable as nutrients or for the treatment of human or animal diseases or for the prevention thereof, for example hormones, polypeptides with immunomodulatory, anti-viral and/or anti-tumor properties (e.g., maspin), antibodies, viral antigens, vaccines, clotting factors, enzyme inhibitors, foodstuffs and the like. Other useful polypeptides that may be produced by the methods of the invention are, for example, those coding for hormones such as secretin, thymosin, relaxin, luteinizing hormone, parathyroid hormone, adrenocorticotropin, melanoycte-stimulating hormone, β-lipotropin, urogastrone or insulin, growth factors, such as epidermal growth factor, insulin-like growth factor (IGF), e.g. IGF-I and IGF-II, mast cell growth factor, nerve growth factor, glia derived nerve cell growth factor, or transforming growth factor (TGF), such as TGFα or TGFβ, e.g. TGFβ1, β2 or β3, growth hormone, such as human or bovine growth hormones, interleukin, such as interleukin-1 or -2, human macrophage migration inhibitory factor (MIF), interferons, such as human α-interferon, for example interferon-αA, αB, αD or αF, β-interferon, γ-interferon or a hybrid interferon, for example an αA-αD- or an αB-αD-hybrid interferon, especially the hybrid interferon BDBB, protease inhibitors such as $α_1$-antitrypsin, SLPI, $α_1$-antichymotrypsin, C1 inhibitor, hepatitis virus antigens, such as hepatitis B virus surface or core antigen or hepatitis A virus antigen, or hepatitis nonA-nonB antigen, plasminogen activators, such as tissue plasminogen activator or urokinase, tumor necrosis factor, somatostatin, renin, β-endorphin, immunoglobulins, such as the light and/or heavy chains of immunoglobulin D, E or G, or human-mouse hybrid immunoglobulins, immunoglobulin binding factors, such as immunoglobulin E binding factor, e.g. sCD23 and the like, calcitonin, human calcitonin-related peptide, blood clotting factors, such as factor IX or VIIIc, erythropoietin, eglin, such as eglin C, desulphatohirudin, such as desulphatohirudin variant HV1, HV2 or PA, human superoxide dismutase, viral thymidine kinase, β-lactamase, glucose isomerase, transport proteins such as human plasma proteins, e.g., serum albumin and transferrin. Fusion proteins of the above may also be produced by the methods of the invention.

Exemplary polynucleotides are those coding for a protease inhibitor, e.g., a human protease inhibitor, or functionally active portion thereof, or a fusion protein of human protease inhibitors or functionally active portions thereof. As used herein, "protease inhibitor" encompasses such fusion proteins comprising more than one protease inhibitor. In one embodiment, the polynucleotide codes for α1-antitrypsin (AAT) or a functionally active portion thereof, or a fusion protein of AAT or a functionally active portion thereof and another protease inhibitor (e.g., a human protease inhibitor) or functionally active portion thereof. Other protease inhibitors that may be produced by means of the invention, either singly or as part of a fusion protein, include, e.g., secretory leukocyte protease inhibitor (SLPI), tissue inhibitor of metalloprotease (TIMP, including TIMP-1, TIMP-2, TIMP-3, and TIMP-4), cystatins, stefins, kininogens, and pepstatin and its analogs. See, e.g., PCT publication No. WO/02/50287; U.S. Publication No.: 2003/0073217A1 (herein incorporated by reference in their entirety) for examples of protease inhibitors and fusions that may be produced by means of the present invention. In the present invention, a "functionally active portion" of a protease inhibitor is a polypeptide that inhibits a protease and that has an amino acid sequence either identical to, or differing in at least one amino acid from, the native form of the protein or a portion of the native form.

As this disclosure makes clear, "portions" refer to functional fragments as one form of variant, as well as variants of full length polypeptide and variants of fragments. The terms protease inhibitor polypetides, such as AAT polypeptide, encompass such embodiments. Accordingly, polypeptides used in the vectors and methods described described herein encompass naturally-occurring (native) and non-naturally occurring sequences and/or forms (including fragments, deletions, etc.). The invention also includes vectors and methods for expressing maspin polypetides and rACT polpeptides.

Methods of testing functionality of polypeptides, such as protease inhibitor polypetides, are known in the art, as well as making fragments and sequence variants. By way of example, the activities of the protease inhibitors may be assessed by means known in the art for each of the individual protease inhibitors; in general, one assays the activity of the appropriate protease in the presence and in the absence of the inhibitor. See, e.g., Barrett, Alan J., ed. Proteolytic enzymes: serine and cysteine peptidases. *Meth Enz* Vol. 244, San Diego, Academic Press, 1994.

This invention also provides embodiments in which an AAT polypeptide (with the requisite functionality) comprises at least about any of the following sequence identities as compared to the sequences for AAT in Table 5: 65%, 70%, 75%, 80%, 85%, 90%, 95%, 98%, or 99%. Two polypeptide sequences are said to be "identical" if the sequence of amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 10 contiguous positions, in some embodiments, at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

For example, the "percentage of sequence identity" may be determined by comparing two optimally aligned sequences over a window of comparison of at least 20 positions, wherein the portion of the polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e. the window size) and multiplying the results by 100 to yield the percentage of sequence identity.

A polypeptide to be produced by the methods of the invention may contain additional sequences. These may include signal sequences (described below), sequences that facilitate purification, and other sequences. For example, additions to the polypeptide chain at the C- or N-terminus may by useful to facilitate purification by, for example, improving expression and facilitating purification (see, for example, U.S. Pat.

No. 6,068,994); such additions are generally cleaved after they have performed their purification assisting function, thus being a part of the DNA coding for the polypeptide but not a part of the final polypeptide. Such additions, as well as others, such as a sequence between the different polypeptides of a fusion protein, can be included in the polypeptides to be produced by the methods of the invention.

As this disclosure makes clear, it is also understood that a polypeptide produced using the vectors and/or methods of the invention may not necessarily display a particular function. The vectors and methods of the invention encompass production of any polypeptide for which production is desired.

E. Optional Signal Sequence

In some embodiments of the invention it is preferable to produce the desired polypeptide intracellularly in order to avoid hyperglycosylation, whereas in other embodiments it is desired that the polypeptide be secreted extracellularly. In the latter embodiments, the plasmid may contain a polynucleotide that encodes, in addition to the desired polypeptide, a signal peptide whose function is to direct the polypeptide to the extracellular space. The DNA sequence encoding the signal peptide (i.e., the "signal sequence" or "leader sequence") is preferably derived from a yeast gene coding for a polypeptide that is ordinarily secreted. Yeast signal sequences are, for example, the signal and prepro sequences of the yeast invertase (SUC2), α-factor, pheromone peptidase (KEX1), "killer toxin" and repressible acid phosphatase (PHO5) genes and the glucoamylase signal sequence from *Aspergillus awamori*. Additional sequences, such as pro- or spacer-sequences which may carry specific processing signals can also be included in the constructions to facilitate accurate processing of precursor molecules. For example, the processing signals contain a Lys-Arg residue, which is recognized by a yeast endopeptidase located in the Golgi membranes.

Examples of signal sequences for protease inhibitors or fusion proteins of protease inhibitors include those from, e.g., AAT (Tables 1 and 2, for DNA and amino acid sequences, respectively) or α-factor signal (yeast) (see Tables 3 and 4, for DNA and amino acid sequences, respectively).

TABLE 1

DNA for leader sequence for human AAT (Kurachi, K. et al., 1981, Proc Natl. Acad. Sci 78, p.6826.)

| | |
|---|---|
| ATGCCGTCTTCTGTCTCGTGGGGCATC-CTCCTGCTGGCAGGCCTGTGCTGCCTGGTCCCT | 60 |
| GTCTCCCTGGCT | 73 |

TABLE 2

Amino acid sequence of leader sequence for human AAT (Kurachi, K. et al., 1981, Proc Natl. Acad. Sci 78, p.6826.)

| | |
|---|---|
| MPSSVSWGILLLAGLCCLVPVSLA | 24 |

TABLE 3

DNA of leader sequence for alpha factor from *S. cerevisiae* (Kurjan, J. and Herskowitz, I., 1982, Cell 30, p. 933)

| | |
|---|---|
| ATGAGATTTCCTTCAATTTTTACTGCAGTTTTATTCGCAGCATCCTCCGCATTAGCTGCT | 60 |
| CCAGTCAACACTACAACAGAAGATGAAACGGCACAAATTCCGGCTGAAGCTGTCATCGGT | 120 |
| TACTCAGATTTAGAAGGGGATTTCGATGTTGCTGTTTTGCCATTTTCCAACAGCACAAAT | 180 |
| AACGGGTTATTGTTTATAAATACTACTATTGCCAGCATTGCTGCTAAAGAAGAAGGGGTA | 240 |
| TCTCTAGATAAAAGAGAGGCTGAAGCTTG | 269 |

TABLE 4

Amino acid sequence of leader sequence for alpha factor from *S. cerevisiae* (Kurjan, J. and Herskowitz, I., 1982, Cell 30, p. 933)

| | |
|---|---|
| MRFPSIFTAVLFAASSALAAPVNTTTEDETAQIPAEAVIGYSDLEGDFDVAVLPFSNSTN | 60 |
| NGLLFINTTIASIAAKEEGVSLDKREAEA | 89 |

F. Construction of the Plasmid

The sequences that make up the plasmid may be joined by conventional techniques. If restriction sites are found outside of functional sequences such as regulatory sequences, coding sequences, or the like, the two sequences may be joined, where the restriction sites are complementary or linkers may be employed for joining the two sequences. The construct may be constructed incrementally, usually employing cloning vectors, where fragments are inserted into the cloning vector stepwise, cloned and the vectors isolated and purified. In one embodiment, the expression vector can be generated from two fragments assembled separately in small, manageable vectors and then ligated and transformed directly into yeast. This method eliminates the need for bacterial sequences required for an *Escherichia coli* shuttle vector, e.g., the bacterial sequences required for propagation and amplification. See, e.g., Zakian and Scott (1982) *Mol Cell Biol* 2:221-32. The use of a shorter vector partially or completely lacking these bacterial sequences decreases the size of the vector and facilitates ease and efficiency of cloning by eliminating one or more cloning steps, thus reducing the time required to produce viable yeast transformants.

If restriction sites are not available outside of functional sequences or inconveniently situated in relation to functional sequences, appropriate restriction sites may be created using PCR primers containing the desired restriction site. Adapters can also be used, which recreate all or a portion of the functional sequence and join together two functional sequences in proper orientation. Various techniques for improving the efficiency with which sequences are joined together include alkaline phosphatase treatment of one sequence; filling in of sequences to provide for blunt end ligation, tailing, or the like.

The yeast promoter, the nucleic acid sequence coding for the signal peptide (if used), the nucleic acid sequence coding for the polypeptide to be produced, the nucleic acid sequence coding for the selectable marker, and the nucleic acid sequence containing yeast transcription termination signals are operably linked to each other. By "operably linked" is meant that the sequences are juxtaposed in such a manner that their normal functions are maintained. For instance, a promoter is operably linked to a coding sequence if the promoter affects its transcription or expression. Generally, operably linked means that the DNA sequences being linked are contiguous and, where necessary to join two polypeptide coding regions, contiguous and in reading frame.

III. Host Cell

The invention concerns furthermore a yeast cell that contains a plasmid (expression vector) as described above. A variety of yeasts can be used; suitable yeasts include those from the genus *Candida, Saccharomyces, Schizosaccharomyces, Pichia, Hansenula, Yarrowia,* and *Kluyveromyces*. Exemplary suitable species are well-known in the art and include, but are not limited to, *Saccharomyces cerevisiae, Pichia pastoris, Hansenula polymorpha,* and *Kluyveromyces lactis*. In some embodiments, a strain of *S. cerevisiae* may be used that lacks the endogenous two micron plasmid (the so-called "circle zero" (cir°) strains) (in some embodiments, a strain that contains the endogenous two micron sequence may be transformed with an expression vector, then cured of its endogenous yeast plasmid), that is deficient in endogenous proteases, such as carboxypeptidase (CpY) and proteinases A and B (PrA and PrB) ("protease-deficient"), and, depending on the selectable marker used, that has a defect in a chromosomal gene coding for an enzyme of amino acid or purine (e.g. uracil) biosynthesis such that insertion of a corresponding intact gene (such as URA3) into the expression vector as described above cures the defect.

In some embodiments, the host cell is a protease-deficient mutant of the yeast *S. cerevisiae*. An exemplary strain for the methods of the invention is strain BJ2168, given the ATCC designation # 208277; for a description see Jones, E. W., *Meth Enz*, vol 185 (Goeddel, ed.), Chapter 31 (1991) and Jones, E. W. *Meth Enz*, vol 194 (Guthrie and Fink, eds.), Chapter 31 (1991). BJ2168 (2168), is a protease-deficient mutant *S. cerevisiae* strain with the following genotype: BJ2168: mat a prc1-407 prb1-1122 pep4-3 leu2 trp1 ura3-52 gal2. This strain may be further modified to a trp revertant by culturing on trp-media, and to cir° by the method of Rose and Broach (*Meth Enz*, vol 185, Goeddel, ed., Chapter 22, 1991) to create strain BJ2168[°]TRP. In some embodiments, the strain is cured of endogenous plasmids after transformation. As is known in the art, the cir° phenotype can be confirmed by Southern blotting or PCR.

The transformation of yeast with the plasmids according to the invention may be accomplished according to methods known in the art. Transformation procedures that may be used to transform yeast cells include electroporation, as described in "Guide to Yeast Genetics and Molecular Biology," Vol. 194 METHODS IN ENZYMOLOGY, C. Guthrie and G. R. Fink, (Academic Press 1991). Other procedures include the transformation of spheroplasts or the transformation of intact cells treated with, e.g., lithium acetate, or calcium chloride, rubidium chloride calcium phosphate, DEAE-dextran, or other substances. Such procedures are described in, for example, Kurtz et al., *Mol. Cell. Biol.* 6:142 (1986); Kunze et al., *J. Basic Microbiol.* 25:141 (1985), for *Candida*; Gleeson et al., *J. Gen. Microbiol.* 132:3459 (1986); Roggenkamp et al., *Mol. Gen. Genet.* 202:302, for *Hansenula* (1986); Das et al., *J. Bacteriol.* 158:1165 (1984); De Louvencourt et al., *J. Bacteriol.* 154:1165 (1983); Van den Berg et al., *Bio/Technology* 8:135 (1990) for *Kluyveromyces*; Cregg et al., *Mol. Cell. Biol.* 5:3376 (1985); Kunze et al., *J. Basic Microbiol.* 25:141 (1985); U.S. Pat. No. 4,837,148 and U.S. Pat. No. 4,929,555, for *Pichia*; Hinnen et al., *Proc. Natl. Acad. Sci. USA* 75:1929 (1978); Ito et al., *J. Bacteriol.* 153:163 (1983), for *Saccharomyces*; Beach and Nurse Nature 300:706 (1981), for *Schizosaccharomyces*; Davidow et al., *Curr. Genet.* 10:39 (1985); Gaillardin et al., *Curr. Genet.* 10:49 (1985), for *Yarrowia*.

An exemplary method of transformation is to transform directly into the yeast strain by the lithium acetate method. Such methods are described in, e.g., Ausebel et al. Vol 2, Chapter 13; Ito et al., above, and Shiestl and Gietz, *Curr. Gent.* 16:339 (1989).

Selected transformants may be plated on selection medium. E.g., if the URA3 gene is used as a selection gene, transformants may be plated on uracil minus plates (Ura– plates) and incubated until viable colonies are visible. Individual transformants may be streaked onto, e.g., Ura– plates and these patches used to inoculate cultures under selection conditions, e.g., Ura–/6% glucose cultures. Transformants may be inoculated into a non-selective medium, such as Yeast Extract Peptone Dextrose.

(YEPD), for shake-flask expression analysis. Cultures may be monitored for growth and analyzed for expression and other characteristics (e.g., solubility) of the desired polypeptide. A clone with the optimal combination of expression and other characteristics may be selected and a glycerol stock prepared for storage in a cell bank Processes for preparation of glycerol stock are well-known. An exemplary process is to grow cells to an optical density (OD) of $\geq 4.0$, then add sterile glycerol to a final concentration of 20%, and freeze the cell bank vials at −80°±10° C. Cells may be stored at −80°±10° C.

IV. Production Process

The methods of the invention encompass the production of proteins, for example, protease inhibitors, or functionally active portions thereof, in yeast.

More generally, the transformed yeast is used according to the methods of the invention to produce the desired polypeptide by culturing the yeast. "Culturing" in the context of the present invention has its usual meaning a person skilled in the art is familiar with, i.e., growing cells that express a desired protein. The specific culture conditions will depend on the cells used and the proteins to be produced and their expression systems. A person skilled in the art of fermentative production of proteins will be familiar with such conditions.

The process is generally divided into two phases. In the batch phase (usually performed in inoculum shake flasks and/or seed fermentor), the cells start growing. In the fed batch phase (which generally occurs in a main fermentor), the cells continue to grow at a controlled rate determined by the feed rate. In embodiments where a promoter is used that is repressed by high levels of a carbon source (e.g., the ADH2 promoter, repressed by glucose), expression of the desired polypeptide is delayed until the fed batch phase, when the carbon source levels drop below levels that repress the promoter. The various parameters of pH, dissolved oxygen, ethanol concentration, carbon source (e.g., glucose) concentration, temperature, culture biomass and growth rate, and the like are measured by standard instrumentation. Monitoring changes in one or more of these parameters provides feedback for maintaining the proper feed rate, which allows buildup of biomass while maintaining specific productivity of the culture.

Preferable sugar or sugar polymers used as the carbon source for polypeptide production include mono-, di-, oligo- or polysaccharide, e.g., glucose (preferably dextrose), fructose, sucrose, maltose, starch, glycogen, or cellulose. The sugar may be pure, or may be part of a sugar containing composition that is a natural or artificially produced syrup, such as molasses, or glucose or fructose syrup. An exemplary sugar is glucose or a glucose-containing composition such as glucose syrup. The sugar or sugar polymer used as the carbon source may make up about 100% of the carbon source used, or as little as about 40%. It is preferable that the sugar or sugar polymer make up about 90% to about 100% of the carbon source, e.g., about 100% of the carbon source.

In the fed batch phase, the feed rate of the carbon source (e.g., glucose), is controlled by controlling feed concentration and/or rate. It is desirable to control the feed concentration and/or rate for the carbon source so that the cells continually deplete the carbon source, while the oxygen levels remain high, so that the cells are maintained in a respiratory state, rather than a fermentative state, thus achieving optimum protein production. As used herein, "feed rate" or "rate of feeding" refers to the rate at which glucose or other carbon source is introduced into the culture medium, and may be adjusted by adjusting the concentration and/or the introduction rate of the feed. In the fed batch phase, the feed rate of the carbon source (e.g., glucose) is monitored and adjusted so that the cells are maintained in the respiratory state. Methods of monitoring the state of the culture to determine if the cells are in the respiratory state include measurements of $CO_2$ evolution and $O_2$ uptake, their ratio expressed as respiratory quotient (RQ), ethanol, and carbon source (e.g., glucose) concentration, pH, dissolved oxygen, biomass concentration and growth rate. Such methods are well-known in the art; see, e.g., Alan Wiseman, editor, *Genetically-Engineered Proteins and Enzymes from Yeast: Production Control* (1991) Ellis Horwood Limited, Chapters 4 and 5. In addition, dissolved oxygen should be continually present during the fed batch phase. The level of dissolved oxygen in the culture medium may be from, e.g., a minimum of about 30% to about 100% saturation, or greater than 50% saturation. The amount of feed depends on the particular batch size and fermentor parameters used, and the adjustment of these is well-known in the art.

For larger production runs, it is preferable to perform the fermentation in stages in which the size of the fermentation vessel is incrementally increased. Normally the fed batch phase of fermentation does not commence until the fermentation is occurring in the largest vessel. Thus, for example, in larger production runs, production of the protein of interest, e.g., rAAT, under the control of a promoter, (e.g., the ADH2 promoter) may start with Fernbach inoculum shake flasks, for example, 2.8 L flasks containing about 600 mL of media, which are seeded with yeast containing a plasmid that codes for the protein of interest under the control of a strong promoter, from a frozen cell bank. After the cell density in the shake flasks has reached optimal levels (e.g., an $OD_{600}$ of between about 2 to about 10, or about 2.5 to about 10), the shake flask is transferred to a seed fermentor. The seed fermentor may have a size between, e.g., 20 to 30 L, and contain between, e.g., about 10 and about 20 L of appropriate medium. After the cell density in the primary seed fermentor has reached optimal levels (e.g., an OD of between 3 and 15), a portion of the contents of the seed fermentor is then transferred to a secondary seed fermentor. The seed fermentor may have a size between, e.g., about 100 to about 200 L, and contain between, e.g., about 65 and about 140 L of appropriate medium. After the cell density in the primary seed fermentor has reached optimal levels (e.g., an OD of between 3 and 15), a portion of the contents of the seed fermentor is then transferred to the main fermentor, which may have a size between, e.g., about 1000 L to about 2000 L, and which may contain between, e.g., about 500 and about 1000 L of medium. The fermentation is stopped in the main fermentor when the levels of desired protein have reached the desired level, by immediate harvest or by cooling to 15° C. at about 50 to about 120 hours after inoculation.

During fermentation, suitable pH modulators, such as, e.g., ammonium hydroxide (25%) or sulfuric acid (15%), are added as necessary to control pH within the desired range. Dissolved oxygen is controlled to ≧about 50% with adjustments of agitation, airflow and backpressure. Antifoam (25%) is added as necessary to control foaming within the Main Fermentor. Throughout the entire main fermentation, carbon source (e.g., glucose) concentration, ethanol concentration and optical density (A600) are measured offline at regular intervals. Samples for measuring expression, wet weight and dry cell weight are taken periodically through the expression period.

This invention also includes compositions comprising the culture media and any of the expression vectors described herein. By way of example, the composition may comprise culture media and one or more yeast cells transformed with the pYEP829 plasmid.

Some embodiments of the invention further include isolation of the protein produced by the yeast. At the end of the fed batch phase, which can be experimentally determined as the time point at which the highest process productivity is reached (polypeptide amount per fermentor volume per process time), the polypeptide is isolated by conventional means, either from the medium if the polypeptide is secreted, or from the cells if it is not. For example, the first step consists usually in lysing the cell wall and removing the cell debris by centrifugation or, in the case of secretory polypeptides, in separating the cells from the culture fluid by means of centrifugation. The resulting supernatant can be enriched for polypeptide by treatment with, e.g. polyethyleneimine so as to remove most of the non-proteinaceous material, and precipitation of the polypeptides by saturating the solution with ammonium sulfate. Host proteins, if present, can also be precipitated, for example, by means of acidification with acetic acid (for example 0.1%, pH 4-5). Other purification steps include, for example, desalination, chromatographic processes, such as ion exchange chromatography gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex column, by affinity chromatography, for example with antibodies, especially monoclonal antibodies. Other methods of protein isolation are well-established in the art. Purified product can be stored in buffers containing e.g. N-acetyl cysteine (NAC), glutathione, cysteine and L-Met that prevent dimerization and oxidation.

The final product may have uses in multiple indications (e.g., rAAT may be used for dermatological, pulmonary, or other disorders), each of which requires a different purity. Depending on the purity desired, different purification methods may be used, as will be apparent to one of skill in the art.

An illustrative embodiment of a process for protease inhibitor production is as follows: Typically, the vector used in such production includes the URA3 gene for selection, a yeast 2 micron DNA sequence, and a polynucleotide encoding a protease inhibitor, such as AAT, alpha one-antichymotrypsin, or maspin. In these embodiments, the polynucleotide encoding the protease inhibitor includes one or more yeast preferred codons substituted for naturally occurring codons, and is operably linked to the alcohol dehydrogenase 2 promoter. The vector is introduced into a yeast cell, for example, a cell of the genus *Saccharomyces* that is cir° and protease deficient. One such cell is the strain BJ2168[°]TRP. The yeast are then grown in a batch phase and a fed batch phase under conditions where dissolved oxygen is continually present in the culture medium throughout the process, and where the glucose feed rate is maintained at a level such that respiratory, rather than fermentative, yeast metabolism is maintained. The fermentation is halted at the desired point, and, in some embodiments, the protease inhibitor is then isolated.

Having described the invention in detail, it will now be illustrated by way of the following Examples. It is understood that the examples and embodiments described herein are for illustrative purposes only and that various modifications or changes in light thereof will be suggested to persons skilled in the art and are to be included within the spirit and purview of this application and scope of the appended claims.

Example 1

Construction of Plasmid pYEP829

This Example describes the construction of the plasmid pYEP829. The plasmid pYEP829 is an episomal expression plasmid that was constructed using ADH2 promoter and terminator sequences, the URA3 gene, and 2 micron sequences cloned de novo by PCR from yeast genomic DNA. It contains the human AAT gene, which was chemically synthesized by Sigma Genosys (The Woodlands, Tex.) using yeast-preferred codons. This yeast codon-based construct was used as a PCR template to generate the chemically synthesized human AAT gene (MetAAT).

The 2 micron sequence in this plasmid contains the origin for autonomous replication in yeast. The URA3 gene facilitates selection of transformed cells and retention of the plasmid during growth in uracil deficient medium. The expression of rAAT is controlled by the glucose-regulated ADH2 promoter. Growth of cells under glucose-limiting conditions induces continuous expression of rAAT and expression is inhibited when cells are grown in excess glucose. The ADH2 terminator is required to terminate transcription of the rAAT gene in yeast.

The plasmid contained no bacterial propagation or amplification sequences.

Several plasmids were constructed to generate the final expression vector, pYEP829, illustrated in FIG. 1.

1. Construction of the rAAT Coding Sequence

The UAATplasmid contains a synthetic rAAT coding sequence cloned into a bacterial cloning vector UBAATplasmid was synthesized using yeast preferred codons and contains ubiquitin (UB) and AAT coding sequences (1421 base pairs combined). This plasmid was used as a PCR template to create the MetAAT gene sequence encoding the rAAT polypeptide sequence. Two PCR primers were used to create the MetAAT gene sequence. Primers AAT-4 and AAT-5 (see below) were used in a primer extension reaction to generate an 1185 bp XbaI/SalI fragment which encoded the entire MetAAT sequence and was cloned into pHG42 Primer AAT-4 contained the XbaI restriction site and Met initiation codon. Primer AAT-5 contained the SalI restriction site. However, this clone had an error resulting in a phenylalanine to leucine change at amino acid 372. To correct this error the XbaI/SalI fragment was subcloned into a bacterial vector. This construct (MetAAT[Leu372]plasmid) served as a template for double-stranded plasmid site-directed mutagenesis. The subcloning step was performed to eliminate the need to sequence the entire expression cassette of pHG42, including the ADH2 promoter and terminator, and the URA3 gene, after the mutagenesis. Primers AAT-11 and AAT-12 were designed to correct the leucine 372 mutation by site-directed plasmid mutagenesis. After double-stranded plasmid site-directed mutagenesis the correct MetAAT sequence (Phe 372) was verified and cloned as an XbaI/SalI fragment into pHG42.

```
PCR Primers:
AAT-4-38
5' GGGCCCTCTAGACCATGGAAGATCCACAAGGTGATGCT 3'

AAT-5-27
5' CCATTGTCGACTACTTTTGGGTTGGG 3'

AAT-11-43
5' GTTCAACAAGCCATTCGTCTTCTTAATGATTGAACAAAACACC 3'

AAT-12-43
5' GGTGTTTTGTTCAATCATTAAGAAGACGAATGGCTTGTTGAAC 3'
```

2. Construction of pHG42 Plasmid

The plasmid pHG42 was constructed to provide several sequences necessary for yeast expression. Plasmid pHG42 contains the URA3 gene which provides a selectable marker in uracil auxotrophic yeast strains, the ADH2 promoter that controls expression of rAAT, and ADH2 transcriptional terminator. The ADH2 promoter, ADH2 terminator and URA3 gene were cloned sequentially into the polylinker of a bacterial plasmid vector, from PCR generated fragments of *S.* cerevisiae genomic DNA, to create pHG41. A shorter promoter was subsequently cloned into pHG41 to make pHG42.

Briefly, the primers ADH2-1 (5' XhoI and BamHI sites) and ADH2-2 (3' XbaI site) were used to amplify and clone the 727 bp ADH2 promoter into a XhoI/XbaI bacterial vector. Next, the 129 bp ADH2 terminator fragment, using primers ADH2-3 (5' XbaI and SalI sites) and ADH2-4 (3' NotI site) was cloned into the XbaI/NotI ADH2 plasmid vector to create pHG40. Primers URA3-1 (5' BamHI site) and URA3-2 (3' XhoI site) were used to generate the 1132 bp URA3 gene by PCR. This was cloned into a BamHI/XhoI pHG40 vector to make pHG41. Finally, a slightly shorter ADH2 promoter (717 bp), using ADH2-1 and ADH2-5 primers, was cloned to replace the original promoter in pHG41 to generate pHG42. This vector was designed to clone the rAAT gene into 5' XbaI and 3' SalI sites.

```
PCR Primers:
ADH2-1-41
5' AGATCTCTCGAGGGATCCAATGCTCTTATCTATGGGACTTC 3'

ADH2-2-30
5' CCTTTCTAGACATTGTGTATTACGATATAG 3'

ADH2-3-44
5' AGATCTTCTAGAAACCTTGTCGACTATGCCTTCACGATTTATAG 3'

ADH2-4-36
5' TTAGATCTGCGGCCGCAACGCGCTGGGAGCAAAAAG 3'

ADH2-5-37
5' GGGCCCTCTAGATTACGATATAGTTAATAGTTGATAG 3'

URA3-1-33
5' GGCCTTGGATCCAGCTTTTCAATTCAATTCATC 3'

URA3-2-31
5' GGCCTTCTCGAGCATTACGACCGAGATTCCC 3'
```

3. Construction of pHG62

Plasmid pHG62 contains the entire 2 micron DNA sequence required for autonomous replication in yeast. The full length yeast 2 micron (2μ) plasmid, B form, was cloned from a *S. cerevisiae* genomic DNA preparation containing 2μ DNA. The unique internal EcoRI site was used to clone the two halves generated by PCR. The 2216 bp NotI/EcoRI fragment (PCR primers 2μ-1 and 2μ-7) and 4009 bp EcoRI/XhoI fragment (PCR primers 2μ-8 and 2μ-2) were cloned into a bacterial plasmid, in a three piece ligation, to create pHG62.

```
PCR Primers:
2μ-1-37
5' TTAGATCTGCGGCCGCTAGGACCCTGCAATTCTTCAAG 3'

2μ-2-46
5' AGGCCTGAGCTCAGATCTCTCGAGCTAACGCTTGTCTTTGTCTC
TG 3'

2μ-7-24
5' TGGCACTTAGAATTCCACGGACTA 3'

2μ-8-24
5' TAGTCCGTGGAATTCTAAGTGCCA 3'
```

4. Construction of the rAAT Expression Plasmid, pYEP829 (FIG. 1)

The rAAT expression cassette (3177 bp) from the MetAATpHG42 plasmid was removed at NotI and XhoI sites for ligation into the NotI/XhoI full length 2μ yeast expression vector (6225 bp) from the pHG62 plasmid. The ligation product pYEP829 (9402 bp), was then transformed into competent yeast (*S. cerevisiae* strain BJ2168).

The entire plasmid was sequenced and the sequence of the rAAT coding region verified by DNA Sequencing using the dideoxy chain termination method. The complete DNA sequence of the plasmid was also analyzed by Restriction Analysis. The sequence is given in Table 5.

TABLE 5

The DNA Sequence for rAAT Production Plasmid pYEP829
Key: The URA3 gene is located at base pairs (bp) 1-1132 and is underlined. The ADH2 promoter is located at bp 1139-1850 and the ADH2 terminator is located at bp 3052-3177. The rAAT coding sequence and corresponding translation in single amino acid code is located at bp 1859-3043. The 2 micron origin of replication is located at bp 3496-4839. Critical restriction sites used in construction of the plasmid are boxed. These restriction sites are XhoI (bp 1-6), BamH1 (bp 1133-1138), XbaI (bp 1851-1856), SalI (bp 3046-3051), NotI (bp 3178-3185), and EcoR1 (bp 5394-5399).

| | |
|---|---|
| `CTCGAG`CATT ACGACCGAGA TTCCCGGGTA ATAACTGATA TAATTAAATT GAAGCTCTAA | 60 |
| TTTGTGAGTT TAGTATACAT GCATTTACTT ATAATACAGT TTTTTAGTTT TGCTGGCCGC | 120 |
| ATCTTCTCAA ATATGCTTCC CAGCCTGCTT TTCTGTAACG TTCACCCTCT ACCTTAGCAT | 180 |
| CCCTTCCCTT TGCAAATAGT CCTCTTCCAA CAATAATAAT GTCAGATCCT CTAGAGACCA | 240 |
| CATCATCCAC GGTTCTATAC TGTTGACCCA ATGCGTCTCC CTTGTCATCT AAACCCACAC | 300 |
| CGGGTGTCAT AATCAACCAA TCGTAACCTT CATCTCTTCC ACCCATGTCT CTTTGAGCAA | 360 |
| TAAAGCCGAT AACAAAATCT TTGTCGCTCT TCGCAATGTC AACAGTACCC TTAGTATATT | 420 |
| CTCCAGTAGA TAGGGAGCCC TTGCATGACA ATTCTGCTAA CATCAAAAGG CCTCTAGGTT | 480 |
| CCTTTGTTAC TTCTTCTGCC GCCTGCTTCA AACCGCTAAC AATACCTGGG CCCACCACAC | 540 |
| CGTGTGCATT CGTAATGTCT GCCCATTCTG CTATTCTGTA TACACCCGCA GAGTACTGCA | 600 |

TABLE 5-continued

The DNA Sequence for rAAT Production Plasmid pYEP829
Key: The URA3 gene is located at base pairs (bp) 1-1132 and is
underlined. The ADH2 promoter is located at bp 1139-1850 and the
ADH2 terminator is located at bp 3052-3177. The rAAT coding sequence
and corresponding translation in single amino acid code is located
at bp 1859-3043. The 2 micron origin of replication is located at bp
3496-4839. Critical restriction sites used in construction of the
plasmid are boxed. These restriction sites are Xho1 (bp 1-6), BamH1
(bp 1133-1138), Xba1 (bp 1851-1856), Sal1 (bp 3046-3051), Not1 (bp
3178-3185), and EcoR1 (bp 5394-5399).

```
ATTTGACTGT ATTACCAATG TCAGCAAATT TTCTGTCTTC GAAGAGTAAA AAATTGTACT    660

TGGCGGATAA TGCCTTTAGC GGCTTAACTG TGCCCTCCAT GGAAAAATCA GTCAAGATAT    720

CCACATGTGT TTTTAGTAAA CAAATTTTGG GACCTAATGC TTCAACTAAC TCCAGTAATT    780

CCTTGGTGGT ACGAACATCC AATGAAGCAC ACAAGTTTGT TTGCTTTTCG TGCATGATAT    840

TAAATAGCTT GGCAGCAACA GGACTAGGAT GAGTAGCAGC ACGTTCCTTA TATGTAGCTT    900

TCGACATGAT TTATCTTCGT TTCCTGCAGG TTTTTGTTCT GTGCAGTTGG GTTAAGAATA    960

CTGGGCAATT TCATGTTTCT TCAACACTAC ATATGCGTAT ATATACCAAT CTAAGTCTGT   1020

GCTCCTTCCT TCGTTCTTCC TTCTGTTCGG AGATTACCGA ATCAAAAAAA TTTCAAGGAA   1080

ACCGAAATCA AAAAAAGAA TAAAAAAAAA TGATGAATTG AATTGAAAAG CT GGATCC AA  1140

TGCTCTTATC TATGGCACTT CCGGGAAACA CAGTACCGAT ACTTCCCAAT TCGTCTTCAG   1200

AGCTCATTGT TTGTTTGAAG AGACTAATCA AGAATCGTT TTCTCAAAAA AATTAATATC    1260

TTAACTGATA GTTTGATCAA AGGGGCAAAA CGTAGGGGCA ACAAACGGA AAAATCGTTT    1320

CTCAAATTTT CTGATGCCAA GAACTCTAAC CAGTCTTATC TAAAAATTGC CTTATGATCC   1380

GTCCCTCCGG TTACAGCCTG TGTAACTGAT TAATCCTGCC TTTCTAATCA CCATTCTAAT   1440

GTTTTAATTA AGGGATTTTG TCTTCATTAA CGGCTTTCGC TCATAAAAAT GTTATGACGT   1500

TTTGCCCGCA GGCGGGAAAC CATCCACTTC ACGAGACTGA TCTCCTCTGC CGGAACACCG   1560

GGCATCTCCA ACTTATAAGT TGGAGAAATA AGAGAATTTC AGATTGAGAG AATGAAAAAA   1620

AAAAAAAAAA AAAAGGCAGA GGAGAGCATA GAAATGGGGT TCACTTTTTG GTAAAGCTAT   1680

AGCATGCCTA TCACATATAA ATAGAGTGCC AGTAGCGACT TTTTTCACAC TCGAAATACT   1740

CTTACTACTG CTCTCTTGTT GTTTTTATCA CTTCTTGTTT CTTCTTGGTA AATAGAATAT   1800

CAAGCTACAA AAAGCATACA ATCAACTATC AACTATTAAC TATATCGTAA TCTAGA CCAT  1860
                                                                    M

GGAAGATCCA CAAGGTGATG CTGCCCAAAA GACCGATACC TCCCACCACG ATCAAGATCA   1920
 E   D   P   Q   G   D   A   A   Q   K   T   D   T   S   H   H   D   Q   D   H

CCCAACCTTC AACAAGATCA CCCCAAACTT GGCTGAATTT GCCTTCTCCT TGTACAGACA   1980
 P   T   F   N   K   I   T   P   N   L   A   E   F   A   F   S   L   Y   R   Q

GTTGGCTCAC CAATCCAACT CCACCAACAT CTTCTTCTCC CCAGTTTCCA TCGCTACTGC   2040
 L   A   H   Q   S   N   S   T   N   I   F   F   S   P   V   S   I   A   T   A

CTTCGCCATG TTGTCCTTGG GTACTAAGGC TGACACTCAC GACGAAATCT TGGAAGGCTT   2100
 F   A   M   L   S   L   G   T   K   A   D   T   H   D   E   I   L   E   G   L

GAACTTCAAC TTGACCGAAA TTCCAGAAGC TCAAATCCAC GAAGGTTTCC AAGAATTGTT   2160
 N   F   N   L   T   E   I   P   E   A   Q   I   H   E   G   F   Q   E   L   L

GAGAACCTTG AACCAACCAG ACTCTCAACT GCAGTTCACC ACCGGTAACG GTTTGTTCTT   2220
 R   T   L   N   Q   P   D   S   Q   L   Q   T   T   G   N   G   L   F   L

GTCCGAAGGT TTGAAGTTGG TTGACAAGTT CTTGGAAGAC GTTAAGAAGT TGTACCACTC   2280
 S   E   G   L   K   L   V   D   K   F   L   E   D   V   K   K   L   Y   H   S

CGAAGCCTTC ACTGTCAACT TCGGTGACAC CGAAGAAGCC AAGAAGCAAA TCAACGACTA   2340
 E   A   F   T   V   N   F   G   D   T   E   E   A   K   K   Q   I   N   D   Y
```

TABLE 5-continued

The DNA Sequence for rAAT Production Plasmid pYEP829
Key: The URA3 gene is located at base pairs (bp) 1-1132 and is
underlined. The ADH2 promoter is located at bp 1139-1850 and the
ADH2 terminator is located at bp 3052-3177. The rAAT coding sequence
and corresponding translation in single amino acid code is located
at bp 1859-3043. The 2 micron origin of replication is located at bp
3496-4839. Critical restriction sites used in construction of the
plasmid are boxed. These restriction sites are Xho1 (bp 1-6), BamH1
(bp 1133-1138), Xba1 (bp 1851-1856), Sal1 (bp 3046-3051), Not1 (bp
3178-3185), and EcoR1 (bp 5394-5399).

```
CGTTGAAAAG GGTACTCAAG GTAAGATTGT GGACTTGGTC AAGGAATTGG ACAGAGACAC    2400
 V  E  K     G  T  Q     G  K  I  V    D  L  V     K  E  L    D  R  D  T

CGTTTTCGCT TTGGTTAACT ACATCTTCTT CAAGGGTAAG TGGCAAAGGC CTTTCGAAGT    2460
 V  F  A     L  V  N     Y  I  F  F    K  G  K     W  R  P     F  E  V

CAAGGACACC GAAGAAGAAG ACTTCCACCT TGACCAAGTT ACCACCGTCA AGGTTCCAAT    2520
 K  D  T     E  E  E     D  F  H  V    D  Q  V     T  T  V     K  V  P  M

GATGAAGAGA TTGGGTATGT TCAACATCCA ACACTGTAAG AAGTTGTCCT CCTGGGTCTT    2580
 M  K  R     L  G  M     F  N  I  Q    H  C  K     K  L  S     S  W  V  L

GTTGATGAAG TACTTGGGTA ACGCCACCGC CATCTTCTTC TTGCCAGACG AAGGTAAGTT    2640
 L  M  K     Y  L  G     N  A  T  A    I  F  F     L  P  D     E  G  K  L

GCAACACTTG GAAAACGAAT TGACCCACGA TATCATCACC AAGTTCTTGG AAAACGAAGA    2700
 Q  H  L     E  N  E     L  T  H  D    I  I  T     K  F  L     E  N  E  D

CAGAAGATCC GCCTCCTTGC ACTTGCCAAA GTTGTCCATT ACTGGTACTT ACGACTTGAA    2760
 R  R  S     A  S  L     H  L  P  K    L  S  I     T  G  T     Y  D  L  K

GTCCGTCTTG GGTCAATTGG GTATCACTAA GGTCTTCTCC AACGGTGCTG ACTTGTCCGG    2820
 S  V  L     G  Q  L     G  I  T  K    V  F  S     N  G  A     D  L  S  G

TGTCACTGAA GAAGCTCCAT TGAAGTTGTC CAAGGCCGTT CACAAGGCTG TCTTGACCAT    2880
 V  T  E     E  A  P     L  K  L  S    K  A  V     H  K  A     V  L  T  I

CGACGAAAAG GGTACTGAAG CTGCTGGTGC CATGTTCTTG GAAGCCATTC CAATGTCTAT    2940
 D  E  K     G  T  E     A  A  G  A    M  F  L     E  A  I     P  M  S  I

CCCACCAGAA GTCAAGTTCA ACAAGCCATT CGTCTTCTTA ATGATTGAAC AAAACACCAA    3000
 P  P  E     V  K  F     N  K  P  F    V  F  L     M  I  E     Q  N  T  K

GTCTCCATTG TTCATGGGTA AGGTTGTCAA CCCAACCCAA AAGTA GTCGA C TATGCCTTC    3060
 S  P  L     F  M  G     K  V  V  N    P  T  Q     K  *

ACGATTTATA GTTTTCATTA TCAAGTATGC CTATATTAGT ATATAGCATC TTTAGATGAC    3120

AGTGTTCGAA GTTTCACGAA TAAAAGATAA TATTCTACTT TTTGCTCCCA GCGCGTT GCG     3180

GCCGC TAGGA CCGGCAATTC TTCAAGCAAT AAACAGGAAT ACCAATTATT AAAAGATAAC    3240

TTAGTCAGAT CGTACAATAA AGCTTTGAAG AAAAATGCGC TTATTCAAT CTTTGCTATA     3300

AAAAATGGCC CAAAATCTCA CATTGGAAGA CATTTGATGA CCTCATTTCT TTCAATGAAG    3360

GGCCTAACGG AGTTGACTAA TGTTGTGGGA AATTGGAGCG ATAAGCGTGC TTCTGCCGTG    3420

GCCAGGACAA CGTATACTCA TCAGATAACA GCAATACCTG ATCACTACTT CGCACTAGTT    3480

TCTCGGTACT ATGCATATGA TCCAATATCA AAGGAAATGA TAGCATTGAA GGATGAGACT    3540

AATCCAATTG AGGAGTGGCA GCATATAGAA CAGCTAAAGG GTAGTGCTGA AGGAAGCATA    3600

CGATACCCCG CATGGAATGG GATAATATCA CAGGAGGTAC TAGACTACCT TTCATCCTAC    3660

ATAAATAGAC GCATATAAGT ACGCATTTAA GCATAAACAC GCACTATGCC GTTCTTCTCA    3720

TGTATATATA TACAGGCAAC ACGCAGATAT AGGTGCGACG TGAACAGTGA GCTGTATGTG    3780

CGCAGCTCGC GTTGCATTTT CGGAAGCGCT CGTTTTCGGA AACGCTTTGA AGTTCCTATT    3840

CCGAAGTTCC TATTCTCTAG AAAGTATAGG AACTTCAGAG CGCTTTTGAA AACCAAAAGC    3900

GCTCTGAAGA CGCACTTTCA AAAACCAAA AACGCACCGG ACTGTAACGA GCTACTAAAA    3960

TATTGCGAAT ACCGCTTCCA CAAACATTGC TCAAAAGTAT CTCTTTGCTA TATATCTCTG    4020
```

TABLE 5-continued

The DNA Sequence for rAAT Production Plasmid pYEP829
Key: The URA3 gene is located at base pairs (bp) 1-1132 and is
underlined. The ADH2 promoter is located at bp 1139-1850 and the
ADH2 terminator is located at bp 3052-3177. The rAAT coding sequence
and corresponding translation in single amino acid code is located
at bp 1859-3043. The 2 micron origin of replication is located at bp
3496-4839. Critical restriction sites used in construction of the
plasmid are boxed. These restriction sites are Xho1 (bp 1-6), BamH1
(bp 1133-1138), Xba1 (bp 1851-1856), Sal1 (bp 3046-3051), Not1 (bp
3178-3185), and EcoR1 (bp 5394-5399).

```
TGCTATATCC CTATATAACC TACCCATCCA CCTTTCGCTC CTTGAACTTG CATCTAAACT    4080

CGACCTCTAC ATTTTTTATG TTTATCTCTA GTATTACTCT TTAGACAAAA AAATTGTAGT    4140

AAGAACTATT CATAGAGTGA ATCGAAACA ATACGAAAAT GTAAACATTT CCTATACGTA     4200

GTATATAGAG ACAAAATAGA AGAAACCGTT CATAATTTTC TGACCAATGA AGAATCATCA    4260

ACGCTATCAC TTTCTGTTCA CAAAGTATGC GCAATCCACA TCGGTATAGA ATATAATCGG    4320

GGATGCCTTT ATCTTGAAAA AATGCACCCG CAGCTTCGCT AGTAATCAGT AAACGCGGGA    4380

AGTGGAGTCA GGCTTTTTTT ATGGAAGAGA AAATAGACAC CAAAGTAGCC TTCTTCTAAC    4440

CTTAACGGAC CTACAGTGCA AAAAGTTATC AAGAGACTGC ATTATAGAGC GCACAAAGGA    4500

GAAAAAAGT AATCTAAGAT GCTTTGTTAG AAAAATAGCG CTCTCGGGAT GCATTTTTGT     4560

AGAACAAAAA AGAAGTATAG ATTCTTTGTT GGTAAAATAG CGCTCTCGCG TTGCATTTCT    4620

GTTCTGTAAA AATGCAGCTC AGATTCTTTG TTTGAAAAAT TAGCGCTCTC GCGTTGCATT    4680

TTTGTTTTAC AAAAATGAAG CACAGATTCT TCGTTGGTAA AATAGCGCTT TCGCGTTGCA    4740

TTTCTGTTCT GTAAAATGC AGCTCAGATT CTTTGTTTGA AAAATTAGCG CTCTCGCGTT     4800

GCATTTTTGT TCTACAAAAT GAAGCACAGA TGCTTCGTTA ACAAAGATAT GCTATTGAAG    4860

TGCAAGATGG AAACGCAGAA AATGAACCGG GGATGCGACG TGCAAGATTA CCTATGCAAT    4920

AGATGCAATA GTTTCTCCAG GAACCGAAAT ACATACATTG TCTTCCGTAA AGCGCTAGAC    4980

TATATATTAT TATACAGGTT CAAATATACT ATCTGTTTCA GGGAAAACTC CCAGGTTCGG    5040

ATGTTCAAAA TTCAATGATG GGTAACAAGT ACGATCGTAA ATCTGTAAAA CAGTTTGTCG    5100

GATATTAGGC TGTATCTCCT CAAAGCGTAT TCGAATATCA TTGAGAAGCT GCAGCGTCAC    5160

ATCGGATAAT AATGATGGCA GCCATTGTAG AAGTGCCTTT TGCATTTCTA GTCTCTTTCT    5220

CGGTCTAGCT AGTTTTACTA CATCGCGAAG ATAGAATCTT AGATCACACT GCCTTTGCTG    5280

AGCTGGATCA ATAGAGTAAC AAAAGAGTGG TAAGGCCTCG TTAAAGGACA AGGACCTGAG    5340

CGGAAGTGTA TCGTACAGTA GACGGAGTAT ACTACTATAG TCTATAGTCC GTG GAATTC T  5400

AAGTGCCAGC TTTATAATGT CATTCTCCTT ACTACAGACC CGCCTGAAAG TAGACACATC    5460

ATCATCAGTA AGCTTTGACA AAAAGCATTG AGTAGCTAAC TCTTCTATGC AATCTATAGC    5520

TGTTTTATAA GGCATTCAAT GGACAGATTG AGGTTTTTGA AACATACTAG TGAAATTAGC    5580

CTTAATCCCT TCTCGAAGTT AATCATGCAT TATGGTGTAA AAAATGCAAC TCGCGTTGCT    5640

CTACTTTTTC CCGAATTTCC AAATACGCAG CTGGGGTGAT TGCTCGATTT CGTAACGAAA    5700

GTTTTGTTTA TAAAAACCGC GAAAACCTTC TGTAACAGAT AGATTTTTAC AGCGCTGATA    5760

TACAATGACA TCAGCTGTAA TGGAAAATAA CTGAAATATG AATGGCGAGA GACTGCTTGC    5820

TTGTATTAAG CAATGTATTA TGCAGCACTT CCAACCTATG GTGTACGATG AAAGTAGGTG    5880

TGTAATCGAG ACGACAAGGG GGACTTTTCC AGTTCCTGAC AATTATAAGA AATACAAAAC    5940

GTTAGCATTT GCATTTGTTG GACATGTACT GAATACAGAC GACACACCGG TAATTGAAAA    6000
```

TABLE 5-continued

The DNA Sequence for rAAT Production Plasmid pYEP829
Key: The URA3 gene is located at base pairs (bp) 1-1132 and is underlined. The ADH2 promoter is located at bp 1139-1850 and the ADH2 terminator is located at bp 3052-3177. The rAAT coding sequence and corresponding translation in single amino acid code is located at bp 1859-3043. The 2 micron origin of replication is located at bp 3496-4839. Critical restriction sites used in construction of the plasmid are boxed. These restriction sites are Xho1 (bp 1-6), BamH1 (bp 1133-1138), Xba1 (bp 1851-1856), Sal1 (bp 3046-3051), Not1 (bp 3178-3185), and EcoR1 (bp 5394-5399).

```
AGAACTGGAT TGGCCTGATC CTGCACTAGT GTACAATACA ATTGTCGATC GAATCATAAA    6060

TCACCCAGAA TTATCACAGT TTATATCGGT TGCATTTATT AGTCAGTTAA AGGCCACCAT    6120

CGGAGAGGGT TTAGATATTA ATGTAAAAGG CACGCTAAAC CGCAGCGGAA AGGGTATCAG    6180

AAGGCCTAAA GGCGTATTTT TTAGATACAT GGAATCTCCA TTTGTCAATA CAAAGGTCAC    6240

TGCATTCTTC TCTTATCTTC GAGATTATAA TAAAATTGCC TCAGAATATC ACAATAATAC    6300

TAAATTCATT CTCACGTTTT CATGTCAAGC ATATTGGGCA TCTGGCCCAA ACTTCTCCGC    6360

CTTGAAGAAT GTTATTAGGT GCTCCATAAT TCATGAATAC ATTTCTAAGT TTGTGGAAAG    6420

AGAACAGGAT AAAGGTCATA TAGGAGATCA GGAGCTACCG CCTGAAGAGG ACCCTTCTCG    6480

TGAACTAAAC AATCTACAAC ATGAAGTCAA TAGTTTAACG GAACAAGATG CGGAGGCGGA    6540

TGAAGGATTG TGGGGTGAAA TAGATTCATT ATGTGAAAAA TGGCAGTCTG AAGCGGAAGA    6600

TCAAACTGAG GCGGAGATAA TAGCCGACAG GATAATTGGA ATAGCCAGA GGATGGCGAA    6660

CCTCAAAATT CGTCCTACAA AGTTCAAAAG TGTCTTGTAT CATATACTAA AGGAACTAAT    6720

TCAATCTCAG GGAACCGTAA AGGTTTATCG CGGTAGTAGT TTTTCACACG ATTCGATAAA    6780

GATAAGCTTA CATTATGAAG AGCAGCATAT TACAGCCGTA TGGGTCTACT TGACAGTAAA    6840

ATTTGAAGAG CATTGGAAGC CTGTTGATGT AGAGGTCGAG TTTAGATGCA AGTTCAAGGA    6900

GCGAAAGGTG GATGGGTAGG TTATATAGGG ATATAGCACA GAGATATATA GCAAAGAGAT    6960

ACTTTTGAGC AATGTTTGTG GAAGCGGTAT TCGCAATATT TTAGTAGCTC GTTACAGTCC    7020

GGTGCGTTTT TGGTTTTTTG AAAGTGCGTC TTCAGAGCGC TTTTGGTTTT CAAAAGCGCT    7080

CTGAAGTTCC TATACTTTCT AGAGAATAGG AACTTCGGAA TAGGAACTTC AAAGCGTTTC    7140

CGAAAACGAG CGCTTCCGAA AATGCAACGC GAGCTGCGCA CATACAGCTC ACTGTTCACG    7200

TCGCACCTAT ATCTGCGTGT TGCCTGTATA TATATATACA TGAGAAGAAC GGCATAGTGC    7260

GTGTTTATGC TTAAATGCGT ACTTATATGC GTCTATTTAT GTAGGATGAA AGGTAGTCTA    7320

GTACCTCCTG TGATATTATC CCATTCCATG CGGGGTATCG TATGCTCCCT TCAGCACTAC    7380

CCTTTAGCTG TTCTATATGC TGCCACTCCT CAATTGGATT AGTCTCATCC TTCAATGCTA    7440

TCATTTCCTT TGATATTGGA TCATACCCTA GAAGTATTAC GTGATTTTCT GCCCCTTACC    7500

CTCGTTGCTA CTCTCCTTTT TTTCGTGGGA ACCGCTTTAG GGCCCTCAGT GATGGTGTTT    7560

TGTAATTTAT ATGCTCCTCT TGCATTTGTG TCTCTACTTC TTGTTCGCCT GGAGGGAACT    7620

TCTTCATTTG TATTAGCATG GTTCACTTCA GTCCTTCCTT CCAACTCACT CTTTTTTTGC    7680

TGTAAACGAT TCTCTGCCGC CAGTTCATTG AAACTATTGA ATATATCCTT TAGAGATTCC    7740

GGGATGAATA AATCACCTAT TAAAGCAGCT TGACGATCTG GTGGAACTAA AGTAAGCAAT    7800

TGGGTAACGA CGCTTACGAG CTTCATAACA TCTTCTTCCG TTGGAGCTGG TGGGACTAAT    7860

AACTGTGTAC AATCCATTTT TCTCATGAGC ATTTCGGTAG CTCTCTTCTT GTCTTTCTCG    7920

GGCAATCTTC CTATTATTAT AGCAAATGAT TTGTATAGTT GCTTTCTATT GTCTAACAGC    7980

TTGTTATTCT GTAGCATCAA ATCTATGGCA GCCTGACTTG CTTCTTGTCA AGAGAGCATA    8040
```

TABLE 5-continued

The DNA Sequence for rAAT Production Plasmid pYEP829
Key: The URA3 gene is located at base pairs (bp) 1-1132 and is
underlined. The ADH2 promoter is located at bp 1139-1850 and the
ADH2 terminator is located at bp 3052-3177. The rAAT coding sequence
and corresponding translation in single amino acid code is located
at bp 1859-3043. The 2 micron origin of replication is located at bp
3496-4839. Critical restriction sites used in construction of the
plasmid are boxed. These restriction sites are Xho1 (bp 1-6), BamH1
(bp 1133-1138), Xba1 (bp 1851-1856), Sal1 (bp 3046-3051), Not1 (bp
3178-3185), and EcoR1 (bp 5394-5399).

```
CCATTTCCAA TCGAATCAAA CCTTTCCTTA ACCATCTTCG CAGCAGGCAA AATTACCTCA   8100
GCACTGGAGT CAGAAGATAC GCTGGAATCT TCTGCGCTAG AATCAAGACC ATACGGCCTA   8160
CCGGTTGTGA GAGATTCCAT GGGCCTTATG ACATATCCTG GAAAGAGTAG CTCATCAGAC   8220
TTACGTTTAC TCTCTATATC AATATCTACA TCAGGAGCAA TCATTTCAAT AAACAGCCGA   8280
CATACATCCC AGACGCTATA AGCTGTACGT GCTTTTACCG TCAGATTCTT GGCTGTTTCA   8340
ATGTCGTCCA TTTTGGTTTT CTTTTACCAG TATTGTTCGT TTGATAATGT ATTCTTGCTT   8400
ATTACATTAT AAAATCTGTG CAGATCACAT GTCAAAACAA CTTTTTATCA CAAGATAGTA   8460
CCGCAAAACG AACCTGCGGG CCGTCTAAAA ATTAAGGAAA AGCAGCAAAG GTGCATTTTT   8520
AAAATATGAA ATGAAGATAC CGCAGTACCA ATTATTTTCG CAGTACAAAT AATGCGCGGC   8580
CGGTGCATTT TTCGAAAGAA CGCGAGACAA ACAGGACAAT TAAAGTTAGT TTTTCGAGTT   8640
AGCGTGTTTG AATACTGCAA GATACAAGAT AAATAGAGTA GTTGAAACTA GATATCAATT   8700
GCACACAAGA TCGGCGCTAA GCATGCCACA ATTTGATATA TTATGTAAAA CACCACCTAA   8760
GGTGCTTGTT CGTCAGTTTG TGGAAAGGTT TGAAAGACCT TCAGGTGAGA AAATAGCATT   8820
ATGTGCTGCT GAACTAACCT ATTTATGTTG GATGATTACA CATAACGGAA CAGCAATCAA   8880
GAGAGCCACA TTCATGAGCT ATAATACTAT CATAAGCAAT TCGCTGAGTT TCGATATTGT   8940
CAATAAATCA CTCCAGTTTA AATACAAGAC GCAAAAAGCA ACAATTCTGG AAGCCTCATT   9000
AAAGAAATTG ATTCCTGCTT GGGAATTTAC AATTATTCCT TACTATGGAC AAAAACATCA   9060
ATCTGATATC ACTGATATTG TAAGTAGTTT GCAATTACAG TTCGAATCAT CGGAAGAAGC   9120
AGATAAGGGA AATAGCCACA GTAAAAAAAT GCTTAAAGCA CTTCTAAGTG AGGGTGAAAG   9180
CATCTGGGAG ATCACTGAGA AAATACTAAA TTCGTTTGAG TATACTTCGA GATTTACAAA   9240
AACAAAAACT TTATACCAAT TCCTCTTCCT AGCTACTTTC ATCAATTGTG GAAGATTCAG   9300
CGATATTAAG AACGTTGATC CGAAATCATT TAAATTAGTC CAAAATAAGT ATCTGGGAGT   9360
AATAATCCAG TGTTTAGTGA CAGAGACAAA GACAAGCGTT AG                     9402
```

Example 2

Yeast Transformation and Selection of Clones

The pYEP829 ligation was transformed directly into the BJ2168-[circle°]TRP yeast strains by the lithium acetate method. Selected transformants were plated on uracil minus plates (Ura– plates) and incubated until viable colonies were visible. Individual transformants were streaked onto Ura– plates and these patches were used to inoculate 3 mL of Ura–/6% glucose cultures. The transformants were inoculated into YEPD, a non-selective medium for shake-flask expression analysis. Cultures were monitored for growth and analyzed for expression and solubility of rAAT at 72 hours. Six transformants of each strain were analyzed and clones selected for preparation of the glycerol stocks. Cells were grown to an optical density (OD) of ≧4.0, then sterile glycerol was added to a final concentration of 20%, and the cell bank vials were frozen at −80°±10° C. One such clone, designated #2E10-10, was used for subsequent fermentation studies.

Alternatively, the pYEP829 ligation mix was transformed directly into BJ2168 and selectively grown on uracil-deficient plates. Transformant colonies were used to inoculate 25 mL shake flask cultures in YEPD medium, grown for 72 hours, and then assayed for production by RP-HPLC and for activity by elastase inhibition assay. Cells were also lysed and separated into soluble and insoluble phases and visualized by SDS-PAGE. The results showed a clone, designated #2B to be the highest producer of rAAT in yeast strain BJ2168. This clone was used to create a glycerol stock for cell storage at −80° C.±10° C.

In order to optimize expression, the #2B glycerol stock was streaked onto a uracil-deficient plate for further selection (Passage 1). Twelve of the resulting colonies were grown in shake flask 25 mL YEPD cultures and analyzed by RP-HPLC, elastase inhibition assay, and SDS-PAGE. The four highest expressers were streaked again as Passage 2, and three of the resulting colonies from each Passage 2 clone were analyzed in shake flasks. The highest producer of AAT in each group of three was streaked again as Passage 3, and three of the resulting colonies from each streak were analyzed in shake flasks. The highest producers of this Passage 3 experiment, #31-1 and #31-9, were similarly used to create glycerol stocks at −80°±10° C.

The 2B#31-9 stock was used to create tryptophan revertants by plating on tryptophan-deficient plates. The revertant colonies were screened in a shake flask experiment (25 mL YEPD medium). The highest expresser of rAAT, 2B#31-9#1A, was grown in the fermentor and exceeded the production levels of 2B#31-9. This new trp revertant subclone was used to create a glycerol stock for storage at −80° C.

The assay data from fermentor experiments are shown in Table 6. Also included are expression level results for the production of recombinant human maspin (Zou et al (1994 Jan. 28) Science 263(5146):526-9) and rACT produced in yeast strain ATCC#208277 (BJ2168), modified to trp revertant and circle 0. All data was accumulated from 5 L fed batch fermentations as described below.

TABLE 6

| Recombinant protein | g recombinant protein/L culture | g cells/L culture (wet weight) | g recombinant protein/ g cells |
| --- | --- | --- | --- |
| rAAT #2E10-10 | 4.2 | 468 | .009 |
| rAAT 2B#31-9#1A | 2.2 | 198 | .011 |
| rMaspin | 2.2 | 499 | .004 |
| rACT | 0.75 | 421 | .002 |

Polymerase Chain Reaction (PCR) Analysis of Endogenous 2 Micron Plasmid Levels in Yeast Production Strains A PCR analysis to detect endogenous 2 micron plasmid and 2 micron production plasmid was developed. This assay uses primers specific to 2 micron DNA sequences that generate different length amplicon fragments from the endogenous vs. production plasmid templates. Thus, a production strain can tested for the presence of endogenous 2 micron plasmid, and confirmed as circle+(presence of 2 micron DNA) or circle 0 (absence of 2 micron DNA). Plasmid DNA was isolated from several yeast samples and analyzed by PCR for presence of 2 micron DNA and/or pYEP829. Four AAT-producing 2B#31-9Trp revertant subclones, 2B#31-9, 2B working cell bank clone, and untransformed yeast strain BJ2168 were all analyzed. The PCR product expected in the presence of 2 micron DNA was produced in untransformed BJ2168 and in unpassaged 2B, but not in any of the passaged subclones. The PCR product expected in the presence of pYEP829 DNA was produced in all passaged subclones but, as expected, was absent from the untransformed BJ2168. These PCR results lead to the conclusion that the passaged subclones were cured of endogenous 2 micron plasmids, i.e. were circle 0.

Example 3

Production of rAAT from pYEP829/2168 by the Fed Batch Process

The recombinant strain of *S. cerevisiae* used was ATCC#208277 (BJ2168), modified to trp revertant and circle 0 (2168[°]TRP), with plasmid pYEP829. Inoculum was prepared from glycerol stock (15-20% glycerol), stored at −70 to −80° C., no special temperature profile during freezing of the culture.

1) Starter Culture 1.1) Shake Flask:

In an appropriate sized flask (i.e. 250 mL), $\frac{1}{10}^{th}$ of seed culture volume, 1:25 thawed, resuspended glycerol stock (1 mL into 25 mL medium) was inoculated. The flask was shaken at 200-250 RPM at 30° C. for 22-28 hrs, until the following criteria were found: OD600: 2.5-6; Glucose: 10-40 g/L; Ethanol: 5-25 g/L. Final samples were taken for a final OD600 reading, and glucose and ethanol concentrations.

2.2) Seed Culture:

Seed culture was prepared in 2.8 L Baffled Fernbach Flasks, to produce $\frac{1}{10}^{th}$ of Production Fermentor Batch Volume. The flask was inoculated at 1:15 with above starter culture and Shaken at 200-250 RPM at 30° C. for 17-20 hrs, until the following transfer criteria were reached: OD600: 2.5-5; Glucose: 20-40 g/L; Ethanol: 5-15 g/L; pH: 2.6-3.1. A final sample was taken for an OD600 reading, glucose and ethanol concentrations, and pH.

The composition of the medium used to produce the starter culture is given in Table 7.

TABLE 7

| Ura- 6% Glucose Medium (Ura-/TV/AAA3/6% D) | | |
| --- | --- | --- |
| Brand (where applicable) | Nutrient | Amount (g/L) |
| Difco | Yeast Nitrogen Base w/o Amino Acids | 6.7 |
| A E Staley Staleydex 333 | Glucose monohydrate (Dextrose) | 60 |
| Ajinomoto | L-alanine | 0.03 |
| Ajinomoto | L-arginine HCl | 0.02 |
| Ajinomoto | L-aspartic acid | 0.02 |
| Ajinomoto | L-glutamic acid | 0.02 |
| Ajinomoto | L-histidine | 0.02 |
| Ajinomoto | L-isoleucine | 0.03 |
| Ajinomoto | L-leucine | 0.1 |
| Ajinomoto | L-lysine | 0.03 |
| Ajinomoto | L-methionine | 0.02 |
| Ajinomoto | L-proline | 0.02 |
| Ajinomoto | L-phenylalanine | 0.05 |
| Ajinomoto | L-serine | 0.02 |
| Ajinomoto | L-threonine | 0.2 |
| Ajinomoto | L-valine | 0.15 |
| Ajinomoto | L-tryptophan | 0.05 |
| Ajinomoto | L-tyrosine | 0.03 |
| Sigma | Thiamine | 0.005 |
| Sigma | Myo-inositol | 0.01 |
| Sigma | Ca-pantothenate | 0.005 |
| Sigma | Choline chloride | 0.1 |
| Sigma | Pyridoxine | 0.0003 |
| Sigma | p-aminobenzoic acid | 0.0002 |
| Sigma | Biotin | 0.00002 |
| Sigma | Riboflavin | 0.0002 |
| Sigma | Folic acid | 0.00002 |
| Sigma | Niacin | 0.0003 |
| J. T. Baker | $(NH_4)_2SO_4$ | 5.0 |

The medium was prepared as follows:

Recipe for IL Ura- 6% Glucose:

6.7 g Difco Yeast Nitrogen Base was dissolved in 836 mL DI water, then autoclaved for 20 min at 121 C. The following ingredients were then added aseptically:

120 mL sterile 50% glucose
10 mL of Ajinomoto AA #3 (100X solution, see recipe, below)
5 mL sterile 1% trp
10 mL sterile 0.3% tyr
0.2 mL sterile Ura- vitamins mix (see recipe, below)
3.6 mL TIPC mix (see recipe, below)
10 mL 50% $(NH_4)_2SO_4$ The medium was mixed well, and stored until use (may be stored up to one week at RT, 2-8° C. for 1 month).

| Ajinomoto AA #3 recipe (100X): | |
|---|---|
| Ingredient | Amount (g) |
| L-alanine | 3.0 |
| L-arginine HCl | 2.0 |
| L-aspartic acid | 2.0 |
| L-glutamic acid | 2.0 |
| L-histidine HCl | 2.0 |
| L-isoleucine | 3.0 |
| L-leucine | 10.0 |
| L-lysine | 3.0 |
| L-methionine | 2.0 |
| L-proline | 2.0 |
| L-phenylalanine | 5.0 |
| L-serine | 2.0 |
| L-threonine | 20.0 |
| L-valine | 15.0 |
| | 73.0 |

Each component was weighed out and the powder was mixed in a coffee grinder. The powder may be stored at RT, covered in foil or in a dark bottle. 7.3 g of powder was dissolved in 100 mL in DI $H_2O$ for a 100× solution (enough for 10 L Ura– media). The mix was sterilized by autoclaving or sterile filtration, and stored at 2-8° C.

Ura- Vitamins Recipe:

1.5 g pyridoxine
1 g p-aminobenzoic acid (PABA)
0.1 g biotin
1 g riboflavin
0.1 g folic acid
1.5 g niacin (nicotinic acid)

The ingredients were weighed out and brought up to 1 L. It did not always completely dissolve. The solution was sterile-filtered through a 0.22 μm filter and stored in dark or aluminum foil covered bottles at 2-8° C.

| TIPC Recipe | |
|---|---|
| Ingredient | Amount |
| 1% (10 g/L) Thiamine | 50 mL |
| 1% (10 g/L) myo-Inositol | 100 mL |
| 5% (50 g/L) Ca-Pantothenate | 10 mL |
| 5% (50 g/L) Choline chloride | 200 mL |

Each component was prepared individually. The components were added to a bottle and the mix was sterilized mix by filtration or autoclaving for 20 mins and stored at 2-8° C.

2) Fermentation
2.1) General Description

Batch media was prepared and sterilized, with post-sterile additions of vitamins. Fermentor was inoculated at a 1:10 dilution (100 mL of inoculum added to 1 L batch medium). Initial glucose and ethanol concentration in the fermentor were a key parameter. When the initial glucose was consumed by the culture, a glucose/nutrient feed was started. The feed rate was designed to keep the glucose concentration at zero and keep the cells from producing ethanol. After the initial ethanol was consumed, conditions were maintained so that there was no measurable glucose or ethanol in the fermentor for the remainder of the run. The fermentation continued for 72 hrs. Oxygen was fed to the fermentor as needed to keep DO2 levels above 50%. Harvest wet weights were in the 450-500 g/L range.

2.2) Growth Parameters

The growth parameters of the fermentation were as follows:

| | |
|---|---|
| pH: | 5.5 with 6% $NH_4OH$ and 2M $H_3PO_4$. Corrected after sterilization, and before inoculation. |
| Agitation: | Variable depending on fermentor. 5 L fermentor with two impellors, initial agitation is 500 RPM. Increase as needed to 700 rpm for DO2 control. |
| $DO_2$: | Kept above 50% with agitation, airflow and $O_2$. Pressure may be used in a suitable tank. |
| Temperature: | 30° C. |
| Airflow: | 1 vvm (SLPM/L). Increased as volume in tank increased. |
| Oxygen: | Started at zero, increased to 20% of airflow as needed for $DO_2$ control. Oxygen tank pressure was the same as fermentor air. |
| Pressure: | 0 psi. in 5 L fermentor, because it is a glass tank so no pressure is used. 0.5-5 psi may be used if tank permits. |
| Time: | 72 hrs |
| Off-line sampling: | 1) $OD_{600\,nm}$ and wet wt. every 8 hours<br>2) Glucose/Ethanol every 2 hours with YSI<br>3) 6 × 2 mL pellets every 8 hrs after 24 hrs EFT |
| Harvest: | By centrifugation with one water wash step. |

2.3) Batch Medium

The composition of the batch medium is given in Table 8.

TABLE 8

| Composition of the batch medium | | |
|---|---|---|
| Brand | Nutrient | Amount (g/L) |
| J. T Baker | $KH_2PO_4$ | 10 |
| J. T Baker | $(NH_4)_2SO_4$ | 3 |
| J. T Baker | Sodium Citrate, Dihydrate | 2.92 |
| J. T Baker | $MgSO_4$ | 0.33 |
| Ajinomoto | Leucine | 0.1 |
| Ajinomoto | Tryptophan | 0.025 |
| Sigma | Choline Chloride | 0.1 |
| Burns Philp OHLY KAT | Yeast Extract | 20 |
| Quest Hy-Soy | Soy Peptone | 20 |
| Sigma | $FeCl_3 \cdot 6H_2O$ | 0.081 |
| J. T Baker | $ZnCl_2 \cdot 4H_2O$ | 0.006 |
| J. T Baker | $CoCl_2 \cdot 2H_2O$ | 0.006 |
| Sigma | $Na_2MoO_4$ | 0.006 |
| Mallinckrodt | $CaCl_2 \cdot 2H_2O$ | 0.003 |
| J. T Baker | $CuSO_4 \cdot 5H_2O$ | 0.0057 |
| Mallinckrodt | $H_3BO_3$ | 0.0015 |
| Sigma | $MnCl_2 \cdot 4H_2O$ | 0.0048 |
| Brose F1 | Antifoam | 53.3 μL |
| Sigma | Myo-inositol | 0.002 |
| Sigma | Thiamine | 0.0005 |

TABLE 8-continued

Composition of the batch medium

| Brand | Nutrient | Amount (g/L) |
|---|---|---|
| Sigma | Riboflavin | 0.00126 |
| Sigma | Folic acid | 0.00012 |
| Sigma | Biotin | 0.00018 |
| Sigma | Niacin | 0.0183 |
| Sigma | Pyridoxine HCl | 0.0042 |
| Sigma | Pantothenic acid | 0.0162 |
| J. T Baker | NaOH | 0.04125 |

Preparation:

Making the initial (batch) media for a 2.5 L starting volume (without the inoculum):

The following were dissolved in 1.5 L DI $H_2O$:

| | | |
|---|---|---|
| 25 g | $KH_2PO_4$ | |
| 7.5 g | $(NH_4)_2SO_4$ | |
| 7.3 g | Sodium Citrate | |
| 0.83 g | $MgSO_4$ | |
| 0.25 g | leucine | |
| 0.063 g | tryptophan | |
| 0.25 g | choline chloride | |
| 50 g | Yeast Extract | |
| 50 g | Soy Peptone | |
| 7.5 mL | Fermentation metals (see recipe, below) | |
| 133 µL | Antifoam | |

The volume was brought to a final volume of 2.5 L with DI $H_2O$. The pH range was measured, and if not within 5.6-6.0, the batch was discarded. The solution was sterilized at 121° C. for 30 minutes.

The following post-sterile additions were made to the 30° C. fermentor:

0.5 mL 1% (10 g/L) myo-inositol
1.25 mL 0.1%(1 g/L) thiamine
5 mL 0.5% choline chloride
7.5 mL Fermentation vitamins mix (see recipe)

Fermentation Metals Recipe (IL):

| Chemical | Amount (g/L) |
|---|---|
| $FeCl_3 \cdot 6H_2O$ | 27.0 |
| $ZnCl_2 \cdot 4H_2O$ | 2.0 |
| $CoCl_2 \cdot 6H_2O$ | 2.0 |
| $Na_2MoO_4$ | 2.0 |
| $CaCl_2 \cdot 2H_2O$ | 1.0 |
| $CuSO_4 \cdot 5H_2O$ | 1.9 |
| $H_3BO_3$ | 0.5 |
| $MnCl_2 \cdot 4H_2O$ | 1.6 |
| Sodium Citrate•$2H_2O$ | 73.5 |

Each ingredient was added to about 900 mL of DI $H_2O$, one at a time until each ingredient was incorporated. Any ingredient that did not fully dissolve at first dissolved completely upon addition of Sodium Citrate. Volume was brought up to 1000 mL with DI $H_2O$. The solution was autoclaved for 30 mins at 121° C., and stored in dark or aluminum foil covered bottles at 2-8° C.

| Vitamin | Amount (g/L) |
|---|---|
| riboflavin | 0.42 |
| folic acid | 0.04 |
| biotin | 0.06 |
| niacin | 6.1 |
| pyridoxine HCl | 1.4 |
| pantothenic acid | 5.4 |
| 50% (500 g/L) NaOH | 27.503 mL |

The vitamins solution was made by mixing three separate solutions together.

Solution A: Riboflavin, folic acid, and biotin were dissolved in 450 mL DI $H_2O$ containing 1.5 mL NaOH and brought up to 500 mL with DI $H_2O$.

Solution B: Niacin and pyridoxine HCl were dissolved in 200 mL DI $H_2O$ containing 26 mL 50% NaOH, and brought up to 250 mL with DI $H_2O$.

Solution C: Pantothenic acid was dissolved in 200 mL DI $H_2O$ containing 0.03 mL 50% NaOH, and brought up to 250 mL with DI $H_2O$. Solutions A, B, and C were combined and sterile filtered through 0.22 µm filter and stored in dark or aluminum foil covered bottle at 2-8° C.

3.4) Feed

The components of the feed are shown in Table 9.

TABLE 9

Feed Components

| Brand | Nutrient | Amount (g/L) |
|---|---|---|
| A E Staley Staleydex 333 | Glucose monohydrate (Dextrose) | 504 |
| J. T Baker | $MgSO_4$ | 1.26 |
| J. T Baker | $KH_2PO_4$ | 3.78 |
| J. T Baker | $(NH_4)_2SO_4$ | 9.45 |
| Ajinomoto | Tryptophan | 0.59 |
| J. T Baker | Sodium citrate, Dihydrate | 1.87 |
| Ajinomoto | Leucine | 2.27 |
| Quest Hy-Soy | Soy Peptone | 31.5 |
| Burns Philp OHLY KAT | Yeast Extract | 126.0 |
| Sigma | $FeCl_3 \cdot 6H_2O$ | 0.1701 |
| J. T Baker | $ZnCl_2 \cdot 4H_2O$ | 0.0126 |
| J. T Baker | $CoCl_2 \cdot 2H_2O$ | 0.0126 |
| Sigma | $Na_2MoO_4$ | 0.0126 |
| Mallinckrodt | $CaCl_2 \cdot 2H_2O$ | 0.0063 |
| J. T Baker | $CuSO_4 \cdot 5H_2O$ | 0.01197 |
| Mallinckrodt | $H_3BO_3$ | 0.00315 |
| Sigma | $MnCl_2 \cdot 4H_2O$ | 0.01008 |
| Sigma | Myo-inositol | 0.0378 |
| Sigma | Thiamine | 0.00063 |
| Sigma | Riboflavin | 0.0026 |
| Sigma | Folic acid | 0.00025 |
| Sigma | Biotin | 0.00038 |
| Sigma | Niacin | 0.0384 |
| Sigma | Pyridoxine HCl | 0.0088 |
| Sigma | Pantothenic acid | 0.0340 |
| J. T Baker | NaOH | 0.0866 |

Preparation:

To make 2.38 L of feed:

Part I:

The following were dissolved in ~300 mL warm DI $H_2O$ on a warm stir plate, without boiling: 1200 g Dextrose (glucose monohydrate), and brought to 1275 mL in DI $H_2O$, then autoclaved at 121° C. for 30 mins. The glucose was allowed to cool to room temperature, then aseptically added to Part II feed. Then part III was added to Part I & II mix (see below).

Part II:
The following were dissolved in ~300 mL DI water on a warm stir plate:

| | | |
|---|---|---|
| 3.0 g | MgSO$_4$ | |
| 9.0 g | KH$_2$PO$_4$ | |
| 22.5 g | (NH$_4$)$_2$SO$_4$ | |
| 1.4 g | tryptophan | |
| 4.44 g | sodium citrate | |
| 5.4 g | leucine | |
| 15 mL | Fermentation metals (see attached) | |
| 75.0 g | Soy Peptone | |
| 300.0 g | Yeast Extract | |

The solution was brought up to 1080 mL with DI H$_2$O and autoclaved in a 5 L bottle (or other feed vessel) with a stir bar at 121° C. for 30 minutes. Part I was added to Part II once they had cooled to about room temperature.

Part III:
The following were aseptically added to the bottle containing room temperature feed Parts I and II:

| | | |
|---|---|---|
| 9.0 mL | 1% (10 g/L) myo-inositol | |
| 1.5 mL | 0.1% (1 g/L) thiamine | |
| 15.0 mL | Fermentation vitamins mix (see recipe) | |

The feed media were placed on a stir plate to incorporate all ingredients, then the pH was measured. If not within range (5.3-5.6), the feed was discarded.

2.4) Feed Rate:
The feed was started when initial glucose was consumed, measured at <0.5 g/L (~EFT 6 hrs). Thereafter the feed rate was adjusted to keep glucose concentrations low enough that respiratory metabolism was maintained and the ADH2 promoter remained de-repressed. The feed rate after 54 hrs was variable, but can be a steady rate if no one is there to watch it overnight. It should be set at a rate that will use all the feed (942 mL/L of batch) by 72 hrs. Total Feed: Feed in 942 mL of feed per liter of batch starting volume.

2.5) Cultivation Time:
72 hours (or until all feed was used up)

2.6) Yield:
Two fed-batch fermentation runs (F5-58 and F5-77) performed using the above protocol generated soluble expression levels of 4.1 and 4.2 g/L as measured by RP-HPLC.

Example 4

Comparison of Yields of rAAT Using Vectors with and without Yeast-Preferred Codons The yield of total soluble AAT produced by transfected yeast were compared when the gene coding for AAT in the expression vector contained yeast-preferred codons compared to when the gene did not contain yeast-preferred codons. In two different vector systems, 42/62 and 42/pYT, the yield of AAT under identical culture conditions was approximately twofold greater using the vectors in which the AAT gene contained yeast-preferred codons (AATyc) compared to the yield in systems where the vector did not contain yeast-preferred codons (AATcDNA)

| Yield of AAT in 42/62 vector system, with and without yeast-preferred codons | | Yield of AAT in 42/pYT vector system, with and without yeast-preferred codons | |
|---|---|---|---|
| AATyc/ 42/62 | 0.17 mg soluble AAT/ml 0.73 units/ml culture | AATyc/ 42/pYT | 0.19 mg soluble AAT/ml 1.11 units/ml culture |
| AATcDNA/ 42/62 | 0.08 mg soluble AAT/ml 0.36 units/ml culture | AATcDNA/ 42/pYT | 0.09 mg soluble AAT/ml 0.36 units/ml culture |

We claim:

1. A vector comprising a selection gene, a yeast 2 micron sequence, and a polynucleotide comprising the nucleic acid sequence SEQ ID NO: 22 encoding an alpha 1-antitrypsin polypeptide, wherein said polynucleotide is operably linked to an alcohol dehydrogenase 2 promoter and a terminator.

2. The vector of claim 1, wherein said vector does not propagate and/or amplify in a bacterial host cell.

3. The vector of claim 1, wherein the selection gene is a URA3 gene.

4. A yeast cell transformed with the vector of claim 1.

5. The yeast cell of claim 4, that is of the genus *Saccharomyces*.

6. The yeast cell of claim 4 that is cir°.

7. The yeast cell of claim 4 that is protease deficient.

8. A vector comprising a URA3 gene, a yeast 2 micron sequence, and a polynucleotide comprising the nucleic acid sequence SEQ ID NO:22 encoding an alpha 1-antitrypsin polypeptide, wherein said polynucleotide is operably linked to an alcohol dehydrogenase 2 promoter and an alcohol dehydrogenase 2 terminator, and wherein said polynucleotide comprises one or more yeast-preferred codons substituted for naturally occurring codons.

9. The vector of claim 8, wherein said vector does not propagate and/or amplify in a bacterial host cell.

10. A yeast cell transformed with the vector of claim 8.

11. The yeast cell of claim 10 that is of the genus *Saccharomyces*.

12. The yeast cell of claim 10 that is cir°.

13. The yeast cell of claim 10 that is protease deficient.

14. A polynucleotide comprising the nucleic acid sequence SEQ ID NO: 22.

15. A vector comprising the polynucleotide of claim 14.

16. The vector of claim 15 further comprising a selection gene.

17. The vector of claim 16 wherein the selection gene is a URA3 gene.

18. The vector of claim 15 further comprising a yeast 2 micron sequence.

19. The vector of claim 15 wherein said polynucleotide is operably linked to an alcohol dehydrogenase 2 promoter and a terminator.

20. The vector of claim 15, wherein said vector does not propagate and/or amplify in a bacterial host cell.

21. A yeast cell transformed with the vector of claim 15.

22. The yeast cell of claim 21, that is of the genus *Saccharomyces*.

23. The yeast cell of claim 21 that is cir°.

24. The yeast cell of claim 21 that is protease deficient.

* * * * *

SEQUENCE LISTING

<160> NUMBER OF SEQ ID NOS: 22

<210> SEQ ID NO 1
<211> LENGTH: 9402
<212> TYPE: DNA
<213> ORGANISM: Artificial Sequence
<220> FEATURE:
<223> OTHER INFORMATION: Description of Artificial Sequence: rAAT
      expression plasmid pYEP829

<400> SEQUENCE: 1

```
ctcgagcatt acgaccgaga ttcccgggta ataactgata taattaaatt gaagctctaa      60
tttgtgagtt tagtatacat gcatttactt ataatacagt tttttagttt tgctggccgc     120
atcttctcaa atatgcttcc cagcctgctt ttctgtaacg ttcaccctct accttagcat     180
cccttccctt tgcaaatagt cctcttccaa caataataat gtcagatcct gtagagacca     240
catcatccac ggttctatac tgttgaccca atgcgtctcc cttgtcatct aaacccacac     300
cgggtgtcat aatcaaccaa tcgtaacctt catctcttcc acccatgtct ctttgagcaa     360
taaagccgat aacaaaatct ttgtcgctct tcgcaatgtc aacagtaccc ttagtatatt     420
```

```
ctccagtaga tagggagccc ttgcatgaca attctgctaa catcaaaagg cctctaggtt    480
cctttgttac ttcttctgcc gcctgcttca aaccgctaac aatacctggg cccaccacac    540
cgtgtgcatt cgtaatgtct gcccattctg ctattctgta tacacccgca gagtactgca    600
atttgactgt attaccaatg tcagcaaatt ttctgtcttc gaagagtaaa aaattgtact    660
tggcggataa tgcctttagc ggcttaactg tgccctccat ggaaaaatca gtcaagatat    720
ccacatgtgt ttttagtaaa caaattttgg gacctaatgc ttcaactaac tccagtaatt    780
ccttggtggt acgaacatcc aatgaagcac acaagtttgt ttgcttttcg tgcatgatat    840
taaatagctt ggcagcaaca ggactaggat gagtagcagc acgttcctta tatgtagctt    900
tcgacatgat ttatcttcgt ttcctgcagg ttttgttct gtgcagttgg gttaagaata    960
ctgggcaatt tcatgtttct tcaacactac atatgcgtat atataccaat ctaagtctgt   1020
gctccttcct tcgttcttcc ttctgttcgg agattaccga atcaaaaaaa tttcaaggaa   1080
accgaaatca aaaaaagaa taaaaaaaaa tgatgaattg aattgaaaag ctggatccaa   1140
tgctcttatc tatgggactt ccgggaaaca cagtaccgat acttcccaat tcgtcttcag   1200
agctcattgt ttgtttgaag agactaatca aagaatcgtt ttctcaaaaa aattaatatc   1260
ttaactgata gtttgatcaa aggggcaaaa cgtaggggca aacaaacgga aaaatcgttt   1320
ctcaaatttt ctgatgccaa gaactctaac cagtcttatc taaaaattgc cttatgatcc   1380
gtccctccgg ttacagcctg tgtaactgat taatcctgcc tttctaatca ccattctaat   1440
gttttaatta agggatttg tcttcattaa cggctttcgc tcataaaaat gttatgacgt   1500
tttgcccgca ggcgggaaac catccacttc acgagactga tctcctctgc cggaacaccg   1560
ggcatctcca acttataagt tggagaaata agagaatttc agattgagag aatgaaaaaa   1620
aaaaaaaaaa aaaaggcaga ggagagcata gaaatggggt tcactttttg gtaaagctat   1680
agcatgccta tcacatataa atagagtgcc agtagcgact tttttcacac tcgaaatact   1740
cttactactg ctctcttgtt gttttttatca cttcttgttt cttcttggta aatagaatat   1800
caagctacaa aaagcataca atcaactatc aactattaac tatatcgtaa tctagaccat   1860
ggaagatcca caaggtgatg ctgcccaaaa gaccgatacc tcccaccacg atcaagatca   1920
cccaaccttc aacaagatca ccccaaactt ggctgaattt gccttctcct tgtacagaca   1980
gttggctcac caatccaact ccaccaacat cttcttctcc ccagtttcca tcgctactgc   2040
cttcgccatg ttgtccttgg gtactaaggc tgacactcac gacgaaatct tggaaggctt   2100
gaacttcaac ttgaccgaaa ttccagaagc tcaaatccac gaaggtttcc aagaattgtt   2160
gagaaccttg aaccaaccag actctcaact gcagttgacc accggtaacg gtttgttctt   2220
gtccgaaggt ttgaagttgg ttgacaagtt cttggaagac gttaagaagt tgtaccactc   2280
cgaagccttc actgtcaact tcggtgacac cgaagaagcc aagaagcaaa tcaacgacta   2340
cgttgaaaag ggtactcaag gtaagattgt ggacttggtc aaggaattgg acagagacac   2400
cgtttttcgct ttggttaact acatcttctt caagggtaag tgggaaaggc ctttcgaagt   2460
caaggacacc gaagaagaag acttccacgt tgaccaagtt accaccgtca aggttccaat   2520
gatgaagaga ttgggtatgt tcaacatcca acactgtaag aagttgtcct cctgggtctt   2580
gttgatgaag tacttgggta acgccaccgc catcttcttc ttgccagacg aaggtaagtt   2640
gcaacacttg gaaaacgaat tgacccacga tatcatcacc aagttcttgg aaaacgaaga   2700
cagaagatcc gcctccttgc acttgccaaa gttgtccatt actggtactt acgacttgaa   2760
gtccgtcttg ggtcaattgg gtatcactaa ggtcttctcc aacggtgctg acttgtccgg   2820
```

```
tgtcactgaa gaagctccat tgaagttgtc caaggccgtt cacaaggctg tcttgaccat    2880
cgacgaaaag ggtactgaag ctgctggtgc catgttcttg gaagccattc caatgtctat    2940
cccaccagaa gtcaagttca acaagccatt cgtcttctta atgattgaac aaaacaccaa    3000
gtctccattg ttcatgggta aggttgtcaa cccaacccaa aagtagtcga ctatgccttc    3060
acgatttata gttttcatta tcaagtatgc ctatattagt atatagcatc tttagatgac    3120
agtgttcgaa gtttcacgaa taaaagataa tattctactt tttgctccca gcgcgttgcg    3180
gccgctagga ccggcaattc ttcaagcaat aaacaggaat accaattatt aaagataac    3240 ttagtcagat cgtacaataa agctttgaag aaaaatgcgc cttattcaat ctttgctata    3300
aaaaatggcc caaatctca cattggaaga catttgatga cctcatttct ttcaatgaag     3360
ggcctaacgg agttgactaa tgttgtggga aattggagcg ataagcgtgc ttctgccgtg    3420
gccaggacaa cgtatactca tcagataaca gcaatacctg atcactactt cgcactagtt    3480
tctcggtact atgcatatga tccaatatca aggaaatga tagcattgaa ggatgagact    3540
aatccaattg aggagtggca gcatatagaa cagctaaagg gtagtgctga aggaagcata    3600 cgatacccg catggaatgg gataatatca caggaggtac tagactacct ttcatcctac    3660
ataaatagac gcatataagt acgcatttaa gcataaacac gcactatgcc gttcttctca    3720
tgtatatata tacaggcaac acgcagatat aggtgcgacg tgaacagtga gctgtatgtg    3780
cgcagctcgc gttgcatttt cggaagcgct cgttttcgga aacgctttga agttcctatt    3840
ccgaagttcc tattctctag aaagtatagg aacttcagag cgcttttgaa aaccaaaagc    3900
gctctgaaga cgcactttca aaaaaccaaa aacgcaccgg actgtaacga gctactaaaa    3960
tattgcgaat accgcttcca caaacattgc tcaaaagtat ctctttgcta tatatctctg    4020
tgctatatcc ctatataacc tacccatcca cctttcgctc cttgaacttg catctaaact    4080
cgacctctac atttttatg tttatctcta gtattactct ttagacaaaa aaattgtagt     4140
aagaactatt catagagtga atcgaaaaca atacgaaaat gtaaacatt cctatacgta     4200 gtatatagag acaaaataga agaaaccgtt cataattttc tgaccaatga agaatcatca    4260
acgctatcac tttctgttca caaagtatgc gcaatccaca tcggtataga atataatcgg    4320
ggatgccttt atcttgaaaa aatgcacccg cagcttcgct agtaatcagt aaacgcggga    4380
agtggagtca ggctttttt atggaagaga aaatagacac caaagtagcc ttcttctaac     4440
cttaacggac ctacagtgca aaaagttatc aagagactgc attatagagc gcacaaagga    4500 gaaaaaagt aatctaagat gctttgttag aaaaatagcg ctctcgggat gcatttttgt     4560
agaacaaaaa agaagtatag attctttgtt ggtaaaatag cgctctcgcg ttgcatttct    4620
gttctgtaaa aatgcagctc agattctttg tttgaaaaat tagcgctctc gcgttgcatt    4680 tttgtttac aaaaatgaag cacagattct tcgttggtaa aatagcgctt tcgcgttgca     4740
tttctgttct gtaaaatgc agctcagatt ctttgtttga aaaattagcg ctctcgcgtt     4800
gcatttttgt tctacaaaat gaagcacaga tgcttcgtta acaaagatat gctattgaag    4860
tgcaagatgg aaacgcagaa aatgaaccgg ggatgcgacg tgcaagatta cctatgcaat    4920
agatgcaata gtttctccag gaaccgaaat acatacattg tcttccgtaa agcgctagac    4980
tatatattat tatacaggtt caaatatact atctgtttca gggaaaactc ccaggttcgg    5040
atgttcaaaa ttcaatgatg ggtaacaagt acgatcgtaa atctgtaaaa cagtttgtcg    5100
gatattaggc tgtatctcct caaagcgtat tcgaatatca ttgagaagct gcagcgtcac    5160
```

```
atcggataat aatgatggca gccattgtag aagtgccttt tgcatttcta gtctctttct    5220
cggtctagct agttttacta catcgcgaag atagaatctt agatcacact gcctttgctg    5280
agctggatca atagagtaac aaaagagtgg taaggcctcg ttaaaggaca aggacctgag    5340
cggaagtgta tcgtacagta gacggagtat actagtatag tctatagtcc gtggaattct    5400
aagtgccagc tttataatgt cattctcctt actacagacc cgcctgaaag tagacacatc    5460
atcatcagta agctttgaca aaaagcattg agtagctaac tcttctatgc aatctatagc    5520
tgttttataa ggcattcaat ggacagattg aggttttga aacatactag tgaaattagc     5580
cttaatccct tctcgaagtt aatcatgcat tatggtgtaa aaaatgcaac tcgcgttgct    5640 ctacttttc ccgaatttcc aaatacgcag ctggggtgat tgctcgattt cgtaacgaaa     5700
gttttgttta taaaaaccgc gaaaaccttc tgtaacagat agattttac agcgctgata     5760 tacaatgaca tcagctgtaa tggaaaataa ctgaaatatg aatggcgaga gactgcttgc    5820
ttgtattaag caatgtatta tgcagcactt ccaacctatg gtgtacgatg aaagtaggtg    5880
tgtaatcgag acgacaaggg ggacttttcc agttcctgac aattataaga aatacaaaac    5940
gttagcattt gcatttgttg gacatgtact gaatacagac gacacaccgg taattgaaaa    6000
agaactggat tggcctgatc ctgcactagt gtacaataca attgtcgatc gaatcataaa    6060
tcacccagaa ttatcacagt ttatatcggt tgcatttatt agtcagttaa aggccaccat    6120
cggagagggt ttagatatta atgtaaaagg cacgctaaac cgcagggaa agggtatcag     6180 aaggcctaaa ggcgtatttt ttagatacat ggaatctcca tttgtcaata caaaggtcac    6240
tgcattcttc tcttatcttc gagattataa taaaattgcc tcagaatatc acaataatac    6300
taaattcatt ctcacgtttt catgtcaagc atattgggca tctggcccaa acttctccgc    6360
cttgaagaat gttattaggt gctccataat tcatgaatac atttctaagt ttgtggaaag    6420
agaacaggat aaaggtcata taggagatca ggagctaccg cctgaagagg acccttctcg    6480
tgaactaaac aatgtacaac atgaagtcaa tagtttaacg gaacaagatg cggaggcgga    6540
tgaaggattg tggggtgaaa tagattcatt atgtgaaaaa tggcagtctg aagcggaaga    6600
tcaaactgag gcggagataa tagccgacag gataattgga aatagccaga ggatggcgaa    6660
cctcaaaatt cgtcgtacaa agttcaaaag tgtcttgtat catatactaa aggaactaat    6720
tcaatctcag ggaaccgtaa aggtttatcg cggtagtagt ttttcacacg attcgataaa    6780
gataagctta cattatgaag agcagcatat tacagccgta tgggtctact tgacagtaaa    6840
atttgaagag cattggaagc ctgttgatgt agaggtcgag tttagatgca agttcaagga    6900
gcgaaaggtg gatgggtagg ttatataggg atatagcaca gagatatata gcaaagagat    6960
acttttgagc aatgttgtg gaagcggtat tcgcaatatt ttagtagctc gttacagtcc     7020
ggtgcgtttt tggttttttg aaagtgcgtc ttcagagcgc ttttggtttt caaaagcgct    7080
ctgaagttcc tatactttct agagaatagg aacttcggaa taggaacttc aaagcgtttc    7140
cgaaaacgag cgcttccgaa aatgcaacgc gagctgcgca catacagctc actgttcacg    7200
tcgcacctat atctgcgtgt tgcctgtata tatatataca tgagaagaac ggcatagtgc    7260
gtgtttatgc ttaaatgcgt acttatatgc gtctatttat gtaggatgaa aggtagtcta    7320
gtacctcctg tgatattatc ccattccatg cggggtatcg tatgctccct tcagcactac    7380
cctttagctg ttctatatgc tgccactcct caattggatt agtctcatcc ttcaatgcta    7440
tcatttcctt tgatattgga tcatacccta gaagtattac gtgattttct gccccttacc    7500
ctcgttgcta ctctcctttt tttcgtggga accgctttag ggccctcagt gatggtgttt    7560
```

-continued

```
tgtaatttat atgctcctct tgcatttgtg tctctacttc ttgttcgcct ggagggaact     7620
tcttcatttg tattagcatg gttcacttca gtccttcctt ccaactcact ctttttttgc     7680
tgtaaacgat tctctgccgc cagttcattg aaactattga atatatcctt tagagattcc     7740
gggatgaata aatcacctat taaagcagct tgacgatctg gtggaactaa agtaagcaat     7800
tgggtaacga cgcttacgag cttcataaca tcttcttccg ttggagctgg tgggactaat     7860
aactgtgtac aatccatttt tctcatgagc atttcggtag ctctcttctt gtctttctcg     7920
ggcaatcttc ctattattat agcaatagat ttgtatagtt gctttctatt gtctaacagc     7980
ttgttattct gtagcatcaa atctatggca gcctgacttg cttcttgtga agagagcata     8040
ccatttccaa tcgaatcaaa cctttcctta accatcttcg cagcaggcaa aattacctca     8100
gcactggagt cagaagatac gctggaatct tctgcgctag aatcaagacc atacggccta     8160
ccggttgtga gagattccat gggccttatg acatatcctg aaagagtag ctcatcagac      8220 ttacgtttac tctctatatc aatatctaca tcaggagcaa tcatttcaat aaacagccga     8280
catacatccc agacgctata agctgtacgt gcttttaccg tcagattctt ggctgtttca     8340
atgtcgtcca ttttggtttt cttttaccag tattgttcgt ttgataatgt attcttgctt     8400
attacattat aaaatctgtg cagatcacat gtcaaaacaa cttttatca caagatagta      8460 ccgcaaaacg aacctgcggg ccgtctaaaa attaaggaaa agcagcaaag gtgcattttt     8520
aaaatatgaa atgaagatac cgcagtacca attattttcg cagtacaaat aatgcgcggc     8580
cggtgcattt ttcgaaagaa cgcgagacaa acaggacaat taaagttagt ttttcgagtt     8640
agcgtgtttg aatactgcaa gatacaagat aaatagagta gttgaaacta gatatcaatt     8700
gcacacaaga tcggcgctaa gcatgccaca atttgatata ttatgtaaaa caccacctaa     8760
ggtgcttgtt cgtcagtttg tggaaaggtt tgaaagacct tcaggtgaga aaatagcatt     8820
atgtgctgct gaactaacct atttatgttg gatgattaca cataacggaa cagcaatcaa     8880
gagagccaca ttcatgagct ataatactat cataagcaat tcgctgagtt tcgatattgt     8940
caataaatca ctccagttta aatacaagac gcaaaaagca acaattctgg aagcctcatt     9000
aaagaaattg attcctgctt gggaatttac aattattcct tactatggac aaaaacatca     9060
atctgatatc actgatattg taagtagttt gcaattacag ttcgaatcat cggaagaagc     9120
agataaggga aatagccaca gtaaaaaaat gcttaaagca cttctaagtg agggtgaaag     9180
catctgggag atcactgaga aaatactaaa ttcgtttgag tatacttcga gatttacaaa     9240
aacaaaaact ttataccaat tcctcttcct agctactttc atcaattgtg gaagattcag     9300
cgatattaag aacgttgatc cgaaatcatt taaattagtc caaataagt atctgggagt       9360 aataatccag tgtttagtga cagagacaaa gacaagcgtt ag                        9402
```

<210> SEQ ID NO 2
<211> LENGTH: 395
<212> TYPE: PRT
<213> ORGANISM: Artificial Sequence
<220> FEATURE:
<223> OTHER INFORMATION: Description of Artificial Sequence: amino acid
      sequence encoded by rAAT expression plasmid pYEP829

<400> SEQUENCE: 2

Met Glu Asp Pro Gln Gly Asp Ala Ala Gln Lys Thr Asp Thr Ser His
1               5                   10                  15

His Asp Gln Asp His Pro Thr Phe Asn Lys Ile Thr Pro Asn Leu Ala
            20                  25                  30

Glu Phe Ala Phe Ser Leu Tyr Arg Gln Leu Ala His Gln Ser Asn Ser
    35                  40                  45

Thr Asn Ile Phe Phe Ser Pro Val Ser Ile Ala Thr Ala Phe Ala Met
 50                  55                  60

Leu Ser Leu Gly Thr Lys Ala Asp Thr His Asp Glu Ile Leu Glu Gly
 65                  70                  75                  80

Leu Asn Phe Asn Leu Thr Glu Ile Pro Glu Ala Gln Ile His Glu Gly
                 85                  90                  95

Phe Gln Glu Leu Leu Arg Thr Leu Asn Gln Pro Asp Ser Gln Leu Gln
            100                 105                 110

Leu Thr Thr Gly Asn Gly Leu Phe Leu Ser Glu Gly Leu Lys Leu Val
        115                 120                 125

Asp Lys Phe Leu Glu Asp Val Lys Lys Leu Tyr His Ser Glu Ala Phe
130                 135                 140

Thr Val Asn Phe Gly Asp Thr Glu Glu Ala Lys Lys Gln Ile Asn Asp
145                 150                 155                 160

Tyr Val Glu Lys Gly Thr Gln Gly Lys Ile Val Asp Leu Val Lys Glu
                165                 170                 175

Leu Asp Arg Asp Thr Val Phe Ala Leu Val Asn Tyr Ile Phe Phe Lys
            180                 185                 190

Gly Lys Trp Glu Arg Pro Phe Glu Val Lys Asp Thr Glu Glu Glu Asp
        195                 200                 205

Phe His Val Asp Gln Val Thr Thr Val Lys Val Pro Met Met Lys Arg
210                 215                 220

Leu Gly Met Phe Asn Ile Gln His Cys Lys Lys Leu Ser Ser Trp Val
225                 230                 235                 240

Leu Leu Met Lys Tyr Leu Gly Asn Ala Thr Ala Ile Phe Phe Leu Pro
                245                 250                 255

Asp Glu Gly Lys Leu Gln His Leu Glu Asn Glu Leu Thr His Asp Ile
            260                 265                 270

Ile Thr Lys Phe Leu Glu Asn Glu Asp Arg Arg Ser Ala Ser Leu His
        275                 280                 285

Leu Pro Lys Leu Ser Ile Thr Gly Thr Tyr Asp Leu Lys Ser Val Leu
290                 295                 300

Gly Gln Leu Gly Ile Thr Lys Val Phe Ser Asn Gly Ala Asp Leu Ser
305                 310                 315                 320

Gly Val Thr Glu Glu Ala Pro Leu Lys Leu Ser Lys Ala Val His Lys
                325                 330                 335

Ala Val Leu Thr Ile Asp Glu Lys Gly Thr Glu Ala Ala Gly Ala Met
            340                 345                 350

Phe Leu Glu Ala Ile Pro Met Ser Ile Pro Pro Glu Val Lys Phe Asn
        355                 360                 365

Lys Pro Phe Val Phe Leu Met Ile Glu Gln Asn Thr Lys Ser Pro Leu
370                 375                 380

Phe Met Gly Lys Val Val Asn Pro Thr Gln Lys
385                 390                 395

<210> SEQ ID NO 3
<211> LENGTH: 72
<212> TYPE: DNA
<213> ORGANISM: Homo sapiens

<400> SEQUENCE: 3
atgccgtctt ctgtctcgtg gggcatcctc ctgctggcag gcctgtgctg cctggtccct    60
gtctccctgg ct                                                         72

<210> SEQ ID NO 4
<211> LENGTH: 24
<212> TYPE: PRT
<213> ORGANISM: Homo sapiens

<400> SEQUENCE: 4

Met Pro Ser Ser Val Ser Trp Gly Ile Leu Leu Ala Gly Leu Cys
1               5                   10                  15

Cys Leu Val Pro Val Ser Leu Ala
            20

<210> SEQ ID NO 5
<211> LENGTH: 269
<212> TYPE: DNA
<213> ORGANISM: Saccharomyces cerevisiae

<400> SEQUENCE: 5
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta      240 tctctagata aaagagaggc tgaagcttg                                       269

<210> SEQ ID NO 6
<211> LENGTH: 89
<212> TYPE: PRT
<213> ORGANISM: Saccharomyces cerevisiae

<400> SEQUENCE: 6

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 7
gggccctcta gaccatggaa gatccacaag gtgatgct                             38

<210> SEQ ID NO 8
<211> LENGTH: 26
<212> TYPE: DNA
<213> ORGANISM: Artificial Sequence

```
<220> FEATURE:
<223> OTHER INFORMATION: Description of Artificial Sequence: Synthetic
      PCR primer

<400> SEQUENCE: 8
ccattgtcga ctactttggg gttggg                                           26

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 9
gttcaacaag ccattcgtct tcttaatgat tgaacaaaac acc                        43

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      pcr primer

<400> SEQUENCE: 10
ggtgttttgt tcaatcatta agaagacgaa tggcttgttg aac                        43

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 11
agatctctcg agggatccaa tgctcttatc tatgggactt c                          41

<210> SEQ ID NO 12
<211> LENGTH: 30
<212> TYPE: DNA
<213> ORGANISM: Artificial Sequence
<220> FEATURE:
<223> OTHER INFORMATION: Dscription of Artificial Sequence: Synthetic
      PCR primer

<400> SEQUENCE: 12
cctttctaga cattgtgtat tacgatatag                                       30

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 13
agatcttcta gaaaccttgt cgactatgcc ttcacgattt atag                       44

<210> SEQ ID NO 14
<211> LENGTH: 36
<212> TYPE: DNA
<213> ORGANISM: Artificial Sequence
<220> FEATURE:
```

```
<223> OTHER INFORMATION: Description of Artificial Sequence: Synthetic
      PCR primer

<400> SEQUENCE: 14
ttagatctgc ggccgcaacg cgctgggagc aaaaag                              36

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 15
gggccctcta gattacgata tagttaatag ttgatag                             37

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16
ggccttggat ccagcttttc aattcaattc atc                                 33

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 17
ggccttctcg agcattacga ccgagattcc c                                   31

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 18
ttagatctgc ggccgctagg accctgcaat tcttcaag                            38

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 19
aggcctgagc tcagatctct cgagctaacg cttgtctttg tctctg                   46

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
                              PCR primer

<400> SEQUENCE: 20
tggcacttag aattccacgg acta                                              24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 21
tagtccgtgg aattctaagt gcca                                              24

<210> SEQ ID NO 22
<211> LENGTH: 1205
<212> TYPE: DNA
<213> ORGANISM: Artificial Sequence
<220> FEATURE:
<223> OTHER INFORMATION: Description of Artificial Sequence: rAAT coding
      sequence with yeast-preferred codons

<400> SEQUENCE: 22
atggaagatc cacaaggtga tgctgcccaa aagaccgata cctcccacca cgatcaagat       60
cacccaacct tcaacaagat caccccaaac ttggctgaat tgccttctc cttgtacaga       120 cagttggctc accaatccaa ctccaccaac atcttcttct ccccagtttc catcgctact      180
gccttcgcca tgttgtcctt gggtactaag gctgacactc acgacgaaat cttggaaggc      240
ttgaacttca acttgaccga attccagaa gctcaaatcc acgaaggttt ccaagaattg       300
ttgagaacct tgaaccaacc agactctcaa ctgcagttga ccaccggtaa cggtttgttc      360
ttgtccgaag gtttgaagtt ggttgacaag ttcttggaag acgttaagaa gttgtaccac     420
tccgaagcct tcactgtcaa cttcggtgac accgaagaag ccaagaagca aatcaacgac    480
tacgttgaaa agggtactca aggtaagatt gtggacttgg tcaaggaatt ggacagagac    540
accgttttcg ctttggttaa ctacatcttc ttcaagggta agtgggaaag gcctttcgaa    600
gtcaaggaca ccgaagaaga agacttccac gttgaccaag ttaccaccgt caaggttcca   660
atgatgaaga gattgggtat gttcaacatc caacactgta agaagttgtc ctcctgggtc   720
ttgttgatga agtacttggg taacgccacc gccatcttct tcttgccaga cgaaggtaag   780
ttgcaacact ggaaaacga attgacccac gatatcatca ccaagttctt ggaaaacgaa    840
gacagaagat ccgcctcctt gcacttgcca agttgtcca ttactggtac ttacgacttg     900
aagtccgtct ggggtcaatt gggtatcact aaggtcttct ccaacggtgc tgacttgtcc   960
ggtgtcactg aagaagctcc attgaagttg tccaaggccg ttcacaaggc tgtcttgacc  1020
atcgacgaaa agggtactga agctgctggt gccatgttct tggaagccat tccaatgtct  1080
atcccaccag aagtcaagtt caacaagcca ttcgtcttct taatgattga acaaaacacc  1140
aagtctccat tgttcatggg taaggttgtc aacccaaccc aaaagtagtc gactatgcct  1200
tcacg                                                               1205
```